United States Patent
Everett et al.

(10) Patent No.: US 10,215,764 B2
(45) Date of Patent: *Feb. 26, 2019

(54) ASSAY REAGENTS FOR A NEUROGRANIN DIAGNOSTIC KIT

(71) Applicant: THE JOHNS HOPKINS UNIVERSITY, Baltimore, MD (US)

(72) Inventors: Allen Dale Everett, Baltimore, MD (US); Jun Yang, Baltimore, MD (US); Zongming Fu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/639,210

(22) Filed: Jun. 30, 2017

(65) Prior Publication Data

US 2017/0315138 A1    Nov. 2, 2017

Related U.S. Application Data

(63) Continuation of application No. 15/280,780, filed on Sep. 29, 2016, now Pat. No. 9,709,578, which is a continuation of application No. 14/117,111, filed as application No. PCT/US2012/037774 on May 14, 2012.

(60) Provisional application No. 61/485,375, filed on May 12, 2011.

(51) Int. Cl.
| | |
|---|---|
| G01N 33/68 | (2006.01) |
| C07K 16/18 | (2006.01) |
| C12N 15/115 | (2010.01) |
| G01N 33/566 | (2006.01) |
| C12Q 1/68 | (2018.01) |

(52) U.S. Cl.
CPC ......... *G01N 33/6896* (2013.01); *C07K 16/18* (2013.01); *C12N 15/115* (2013.01); *C12Q 1/68* (2013.01); *G01N 33/566* (2013.01); *C07K 2317/30* (2013.01); *C12N 2310/16* (2013.01); *G01N 2333/47* (2013.01); *G01N 2800/28* (2013.01)

(58) Field of Classification Search
None
See application file for complete search history.

(56) References Cited

U.S. PATENT DOCUMENTS

| | | |
|---|---|---|
| 6,780,606 B1 | 8/2004 | Jackowski |
| 7,396,654 B2 | 7/2008 | Hayes |
| 7,427,490 B2 | 9/2008 | Valkirs |
| 2003/0224460 A1 | 12/2003 | Pedersen et al. |
| 2004/0014143 A1 | 1/2004 | Haskins et al. |
| 2006/0257943 A1 | 11/2006 | Dambinova |
| 2007/0098728 A1 | 5/2007 | Pedersen et al. |
| 2008/0026485 A1 | 1/2008 | Hueber et al. |
| 2008/0131881 A1 | 6/2008 | Ladenson et al. |
| 2008/0220013 A1 | 9/2008 | Hochstrasser et al. |
| 2009/0068691 A1 | 3/2009 | Dave et al. |
| 2011/0207126 A1 | 8/2011 | Popko et al. |
| 2013/0252834 A1 | 9/2013 | Dayon et al. |
| 2014/0141458 A1 | 5/2014 | Everett |

FOREIGN PATENT DOCUMENTS

| | | |
|---|---|---|
| WO | 2006/012351 | 2/2006 |
| WO | 2008/046509 | 4/2008 |
| WO | 2009/143519 | 11/2009 |
| WO | 2010/019553 | 2/2010 |
| WO | 2012/155134 | 11/2012 |

OTHER PUBLICATIONS

Berger et al., "The Use of Biomarkers After Inflicted Traumatic Brain Injury: Insight Into Etiology, Pathophysiology, and Biochemistry," Clin Ped Emer Med, vol. 7(3), pp. 186-193 (2006).

Clayton, D., et al., "Conservation and expression of IQ-domain-containing calpacitin gene products (neuromodulin/GAP-43, neurogranin/RC3) in the adult and developing oscine song control system", Developmental Neurobiology, Feb. 1, 2009, vol. 69, No. 2-3, pp. 124-140.

Haqqani et al., "Biomarkers and diagnosis; protein biomarkers in serum of pediatric patients with severe traumatic brain injury identified by ICAT-LC-MS/MS" J. Neurotrauma, vol. 24(1), pp. 54-74 (2007).

Hergenroeder et al.; "Biomarkers in the clinical diagnosis and management of traumatic brain injury," Mol Diagn Ther., vol. 12(6), pp. 345-358 (2008).

Hoehna, Y. et al., "Matrix metalloproteinase 9 regulates cell death following pilocarpine-induced seizures in the developing brain," Neurobiology of Disease, vol. 48, pp. 339-347 (2012).

Hoshi, T. et al., "Relations of serum high sensitivity c-reactive protein and interleukin-6 levels with silent brain infarction," Stroke, vol. 36, No. 4 (2005), pp. 768-772.

Iliuk, A., et al., "Aptamer in Bioanalytical applications," Analytical Chemistry, vol. 83, pp. 4440-4452 (2011).

Ishigami, A. et al. "Abnormal accumulation of citrullinated proteins catalyzed by peptidylarginine deiminase in hippocampal extracts from patients with alzheimer's disease," Journal of Neuroscience Research, vol. 80, pp. 120-128 (2005).

Koumura, A., et al., "Metallothionein-3 deficient mice exhibit abnormalitites of physchological behaviors," Neuroscience Letters, vol. 467, pp. 11-14 (2009).

(Continued)

*Primary Examiner* — Adam Weidner
(74) *Attorney, Agent, or Firm* — Melissa Hunter-Ensor; Leslie Serunian; Greenberg Traurig, LLP

(57) ABSTRACT

The present invention relates to the field of biomarkers. More specifically, the present invention relates to assay reagents useful in detecting neurogranin. In a specific embodiment, the present invention provides an isolated antibody or fragment thereof that specifically binds to neurogranin. In another embodiment, the present invention provides a polynucleotide aptamer that specifically binds neurogranin.

15 Claims, 9 Drawing Sheets

Specification includes a Sequence Listing.

(56) References Cited

OTHER PUBLICATIONS

Laterza, O. et al., "Biomarkers of tissue injury," Biomarkers Med., vol. 2, No. 1, pp. 81-92 (2008).
Laterza, O. et al., "Identification of novel brain biomarkers," Clinical Chemistry, American Association for Clinical Chemistry, Washington, DC, Sep. 1, 2006, vol. 52, No. 9, pp. 1713-1721.
Merck "Product 07-425" Accessed from www.merckmillipore.com on May 26, 2015.
NCBI GeneBank Accession No. NP_006167 (Jan. 14, 2011).
Neuner-Jehle, M. et al., Sleep Deprevation differentially alters the mRNA and protein levels of neurogranin in rat brain, Brain Research, Jul. 1, 1995, vol. 685, No. 1-2, pp. 143-153.
Oguz, K. et al., "Assessment of citrullinated myelin by 1H-MR spectroscopy in early-onset multiple sclerosis," American Journal of Neuroradiol, vol. 30, pp. 716-721 (2009).
Oliveira, C. et al., "Outcome biomarkers following severe traumatic brain injury," Rev Bras Ter Intensiva, vol. 20, No. 4, pp. 411-421 (2008).
Ottens et al., "Neuroproteomics in neurotrauma," Mass Spectrom Rev. May-Jun. 2006; vol. 25(3): pp. 380-408.
Pak, J., et al., "Involvement of neurogranin in the modulation of calcium/calmodulin-dependent protein kinase II, synaptic plasticity, and spatial learning: a study with knockout mice," Proc. Natl. Acad. Sci. USA, Oct. 10, 2000, vol. 97, No. 21, pp. 11232-11237.
Pegelow et al., "Silent infarcts in children with sickle cell anemia nad abnormal cerebral atery volocity," Arch Neurol. Dec. 2001; vol. 58(12), pp. 2017-2021.
Radka, S. et al., "Presence of brain derived neurotrophic factor in brain and human and rate but not mouse serum detected bu a sensitive and specific immuoassay," Brain Research, vol. 708, pp. 122-130 (1996).
Savage, W. et al., "Plasma glial fibrillary acidic protein levels in children with sickle cell disease," American Journal of Hematology, vol. 86, No. 5 (2011), pp. 427-429.
Tang, L., et al., "Attenuation of opiod tolerance by antisense oligodeoxynucleotides targeting neurogranin," European Journal of Pharmacology, vol. 542, pp. 106-107 (2006).
Tang, L., et al., "Disruption of acute opiod dependence bu antisense oligodeoxynucleotides targeting neurogranin," Brain Research, vol. 1143, pp. 78-82 (2007).
Thorsell, A. et al., "Neurogranin in cerebrospinal fluid as a marker of synaptic degeneration in Alzheimer's Disease," Brain Research, vol. 1362, pp. 13-22 (2010).
Tok, J., et al., "Single microbead SELEX for efficient ssDNA aptamer generation against botulinum neurotoxin," Chem. Commun., Mar. 18, 2008, pp. 1883-1885.
Vendt et al., "Silent Cerebral Transfusion (SIT) trial imaging core: application of novel imaging information technology for rapid and central review of MRI of the brain," J Digit Imaging. Jun. 2009; vol. 22(3), pp. 26-43.
Wang et al., "MRI Abnormalities of the brain in one-year-old children with sickle cell anemia," Pediatr Blood Cancer, Nov. 2008; vol. 51(5): pp. 643-646, doiL 10.1002/pbc.21612.2008.
Watson, J. et al., "Localization of RC3 (neirogranin) in rat brain subcellular fractions," Molecular Brain Research, Dec. 1, 1994, vol. 27, No. 2, pp. 323-328.
Williams, L., et al., "Proteomic-based approach for biomarker discovery to predict silent cerebral infant in patients with sickle cell disease," 51st Annual meeting of the American Society of Hematology, New Orleans, LA (2009).
Wu, L. et al., "Characterization, using coparative proteomics, of differentially expressed proteings in the hippocampus of the mesial temporal lobe of epileptic rats following treatment with valproate," Amino Acids, vol. 40, pp. 221-238 (2011).
Zeterberg, H., et al., "Nerochemical aftermath of amateur boxing," Arch Neurol., vol. 63, pp. 1277-1280 (2006).
Zhang, H. et al., "Methods for Peptide and protein quantitation by liquid chromatography-multiple reaction monitoring mass spectrometry," Molecular and Cellular Proteomics, pp. 1-62 (2011).
Extended European Search Report dated Feb. 10, 2014 for EP application 11833480.
European Search Report dated Oct. 9, 2015 for EP Application No. 13760865.
European Search Report dated Jul. 13, 2015 for EP Application 12782967.
Communication pursuant to Article 94(3) EPC in corresponding European Patent Application No. 12 782 967.9, dated Dec. 12, 2017 (4 pages).
Communication pursuant to Article 94(3) EPC, dated Nov. 2, 2018, as received in corresponding European Patent Application No. 12 782 967.9 (4 pages).

ASSAY REAGENTS FOR A NEUROGRANIN DIAGNOSTIC KIT

CROSS-REFERENCE TO RELATED APPLICATIONS

This application is a continuation of patent application U.S. Ser. No. 15/280,780, filed on Sep. 29, 2016, now allowed, which is a continuation of patent application U.S. Ser. No. 14/117,111, filed Jan. 17, 2014, which is a U.S. National Stage Application under 35 U.S.C. § 371 of International PCT Application No. PCT/US2012/037774, having an international filing date of May 14, 2012, which claims the benefit of U.S. Provisional Application No. 61/485,375, filed May 12, 2011, the contents of all of which are incorporated herein by reference in their entireties.

STATEMENT OF GOVERNMENTAL INTEREST

This invention was made with U.S. government support under grant no. NHLBI 1 R01 HL091759-02, and NHLBI 5U54HL090515-02. The U.S. government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "P11546-02_Sequence_Listing_ST25.txt." The sequence listing is 3,146 bytes in size, and was created on May 10, 2012. It is hereby incorporated by reference in its entirety.

FIELD OF THE INVENTION

The present invention relates to the field of biomarkers. More specifically, the present invention relates to assay reagents useful in detecting biomarkers.

BACKGROUND OF THE INVENTION

Brain injuries are complex and can have multiple severe clinical outcomes. Injury of the brain and spinal cord can result from head trauma, stroke, traumatic birth, heart surgery, cardiac arrest and patients requiring cardiovascular support with ventricular assist devices or extracorporeal membrane oxygenation (ECMO). Moreover, detection of subclinical brain injury is difficult, especially in children and neonates with birth-related injury. In addition, children with sickle cell disease are at high risk for subclinical brain injury. Untreated subclinical brain injuries in children can progress to overt stroke, neurological damage, learning problems and memory loss.

Unfortunately, clinical tools such as physical exam, and imaging (CT Scan or MRI) are subjective, not widely available, not sensitive or specific enough and or too costly to identify the infant, child or adult with brain injury. There is a great clinical need to identify patients with brain injury and especially subclinical injury because these infants, children and adults are at significant risk of progressing to overt stroke and development of cognitive and motor loss, and dementia.

SUMMARY OF THE INVENTION

The present invention is based, at least in part, on the development of aptamers and antibodies that bind neurogranin. In one embodiment, the present invention provides an isolated antibody or fragment thereof that specifically binds to neurogranin. In a specific embodiment, the isolated antibody or fragment thereof specifically binds to amino acids 1-78 of SEQ ID NO:4. In a more specific embodiment, an isolated antibody or fragment thereof specifically binds to amino acids 55-78 of SEQ ID NO:4. In certain embodiments, the antibody or fragment thereof is polyclonal. In other embodiments, the antibody or fragment thereof is monoclonal. In a specific embodiment, the antibody or fragment thereof is mammalian. The antibody or fragment thereof can be human. In particular embodiments, the present invention provides a hybridoma cell which produces the antibody or fragment described herein.

The antibody fragment can be selected from the group consisting of a Fab fragment; a F(ab') 2 fragment; a Fv fragment; and a single chain fragment. The isolated antibody or fragment thereof can further comprise a detectable substance coupled to the antibody. In certain embodiments, the detectable substance is selected from the group consisting of an enzyme; a fluorescent label; a radioisotope; and chemiluminescent label.

In one embodiment, the isolated antibody or fragment thereof specifically binds to neurogranin in an ELISA. In another embodiment, the isolated antibody or fragment thereof specifically binds to neurogranin in a competitive-binding assay. In yet another embodiment, the isolated antibody or fragment thereof specifically binds to neurogranin in a radioimmunoassay. In a further embodiment, the isolated antibody or fragment thereof specifically binds to neurogranin in a fluorescence-activated cell sorting (FACS) assay.

In another aspect, the present invention provides kits useful for detecting neurogranin. A kit for detecting neurogranin may comprise (a) an isolated antibody described herein; and (b) at least one component to detect binding of the isolated antibody to neurogranin.

In another embodiment, the present invention provides an isolated antibody obtained from an animal that has been immunized with neurogranin, wherein the antibody specifically binds to an antigenic epitope-bearing polypeptide fragment of neurogranin. In an specific embodiment, the present invention provides a monoclonal antibody designated 30.5.2 that specifically binds neurogranin, and is produced by the cell line designated "NRGN Clone 30.5.2," which was deposited with the American Type Culture Collection (ATCC®), Manassas, Va., 20108, USA, on Sep. 7, 2016, under ATCC Designation No. PTA-123496. The deposit was made pursuant to the provisions of the Budapest Treaty on the International Recognition of the Deposit of Material for the Purposes of Patent Procedure (Budapest Treaty). In another embodiment, the present invention provides an anti-neurogranin monoclonal antibody which is produced by a hybridoma.

In another aspect, the present invention provides aptamers that bind neurogranin. In certain embodiments, the present invention provides a polynucleotide aptamer that specifically binds neurogranin. In another embodiment, the neurogranin is human neurogranin. In a specific embodiment, the aptamer binds to neurogranin with a Kd of less than about 1000 nM. In a more specific embodiment, the aptamer binds to neurogranin with a Kd of less than about 100 nM. In a further embodiment, the aptamer binds to neurogranin with a Kd of less than about 20 nM. The polynucleotide aptamer of the present invention can consist of about 10 to about 100 nucleotides. In another embodiment, the polynucleotide aptamer consists of about 20 to about 80 nucleotides. In yet another embodiment, the polynucleotide aptamer consists of about 30 to about 50 nucleotides. In particular embodiments, the polynucleotide aptamer is an RNA aptamer.

In a specific embodiment, the polynucleotide aptamer comprises a nucleotide sequence at least 80% identical to any one of SEQ ID NOS: 4-6 or a fragment thereof of at least ten contiguous nucleotides. In another embodiment, the polynucleotide aptamer comprises a nucleotide sequence at least 90% identical to any one of SEQ ID NOS: 4-6 or a fragment thereof of at least ten contiguous nucleotides. In yet another embodiment, the polynucleotide aptamer comprises a nucleotide sequence at least 95% identical to any one of SEQ ID NOS: 4-6 or a fragment thereof of at least ten contiguous nucleotides.

In another embodiment, a polynucleotide aptamer comprises the nucleotide sequence of any one of SEQ ID NOS: 4-6 or a fragment thereof of at least ten contiguous nucleotides. In a further embodiment, a polynucleotide aptamer consists of the nucleotide sequence of any one of SEQ ID NOS: 4-6 or a fragment thereof of at least ten contiguous nucleotides. The polynucleotide aptamer can comprise at least one modified internucleotide linker. In other embodiments, the polynucleotide aptamer can comprise at least one terminal blocker. The polynucleotide aptamer of the present invention can be linked to a conjugate.

The present invention further provides a polynucleotide encoding a polynucleotide aptamer described herein. In a specific embodiment, the present invention provides a vector comprising a polynucleotide described herein. The present invention further provides a cell comprising a polynucleotide aptamer described herein. A cell may comprise two or more different polynucleotide aptamers. The present invention also provides a polynucleotide described herein, as well as a vector described herein.

In another aspect, the present invention provides methods of diagnosing a disease or disorder associated with neurogranin in a subject. In certain embodiments, the method comprises measuring the level of neurogranin in the subject by binding neurogranin with a polynucleotide aptamer and determining the amount of aptamer bound to neurogranin. In a particular embodiment, the binding occurs in a sample obtained from the subject. In other embodiments, a method for determining the amount of neurogranin in a sample comprises the step of detecting a peptide specific to neurogranin using a triple quadrupole mass spectrometer and multiple reaction monitoring, wherein the peptide specific to neurogranin comprises SEQ ID NO: 7.

In a specific embodiment, the present invention provides a neurogranin RNA aptamer (NRGN-A1) with a sequence comprising the sequence of:
TCTAACGCCTCCCGTATGTTTTCCTTTTTCCATT-GCGGAT (SEQ ID NO: 4), which can bind to neurogranin protein and is useful for a detection assay. In another embodiment, the present invention provides a neurogranin RNA aptamer (NRGN-A6) with a sequence comprising the sequence of:
TTTTCATTTTCATTTTTTTCCAAATCGATCCGCCG-GACCTTAT (SEQ ID NO: 6), which can bind to neurogranin protein and is useful for a detection assay.

In another embodiment, the present invention provides a monoclonal antibody identified as 30.5.2 (ATCC Deposit Designation PTA-123496) to human neurogranin and is useful for a diagnostic detection assay for brain injury. In a further embodiment, a method of using a neurogranin RNA aptamer in a diagnostic assay for brain injury in a mammalian subject, comprises the steps of (a) obtaining a sample from the subject suspected of having a brain injury, and (b) performing an assay using the aptamer to detect a level of neurogranin in the sample, wherein a level of neurogranin in the sample that is significantly different than in a sample obtained from a control subject that does not have a brain injury is diagnostic of a brain injury. In yet another embodiment, a method of using a neurogranin monoclonal antibody in a diagnostic assay for brain injury in a mammalian subject, comprises the steps of (a) obtaining a sample from the subject suspected of having a brain injury, and (b) performing an assay using the antibody to detect the level of neurogranin in the sample, wherein a level of neurogranin in the sample that is significantly different than in a sample obtained from a control subject that does not have a brain injury is diagnostic of a brain injury. In such methods, the brain injury is selected from the group consisting of subclinical brain injury and overt brain injury. Finally, the present invention provides a diagnostic/prognostic kit for brain injury comprising capture and detection reagents for neurogranin.

DETAILED DESCRIPTION OF THE INVENTION

Figure 1:
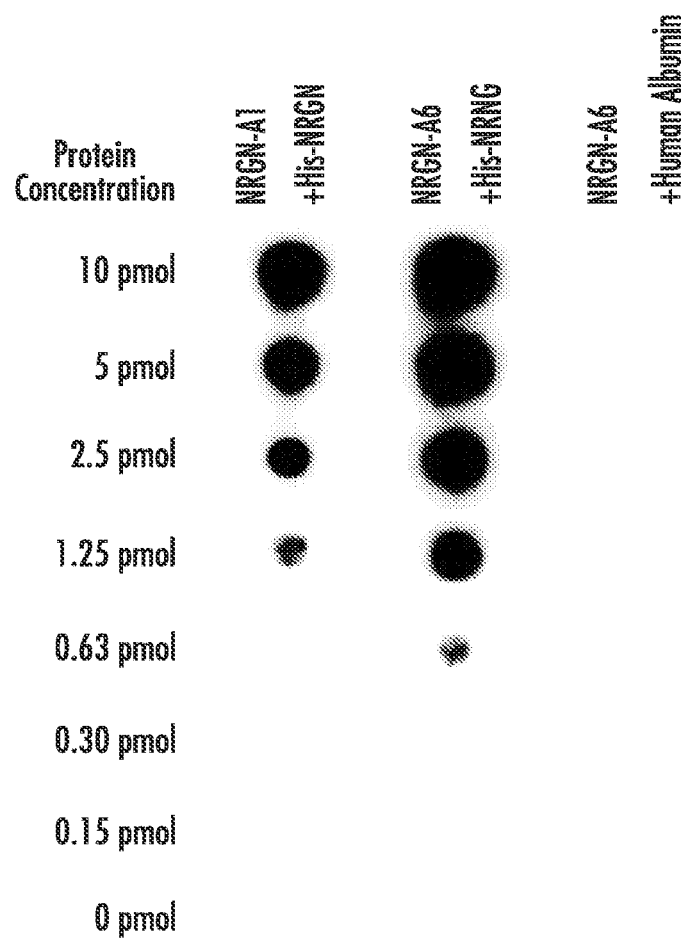
FIG. 1 is a gel showing the minimum amount of neurogranin aptamers needed to for detection of neurogranin protein.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as an impact (percussive) or a biological abnormality such as a stroke resulting from either blockage or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury. A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, and the like).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, and medications, particularly sedation and anesthesia.

The term "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels that correspond to, for example, a patient having subclinical brain injury (SCI), not having SCI, is responding to treatment for SCI, is not responding to treatment for SCI, is/is not likely to respond to a particular SCI treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels of the same biomarkers in a control sample (e.g., predefined levels that correlate to uninfected individuals, standard SCI levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has SCI. In specific embodiments, the parameter may comprise the level of one or more biomarkers of the present invention. A particular set or pattern of the amounts of one or more biomarkers may indicate that a patient has SCI (i.e., correlates to a patient having SCI). In other embodiments, a particular set or pattern of the amounts of one or more biomarkers may be correlated to a patient being unaffected (i.e., indicates a patient does not have SCI). In certain embodiments, "indicating," or "correlating," as used according to the present invention, may be by any linear or non-linear method of quantifying the relationship between levels of biomarkers to a standard, control or comparative value for the assessment of the diagnosis, prediction of SCI or SCI progression, assessment of efficacy of clinical treatment, identification of a patient that may respond to a particular treatment regime or pharmaceutical agent, monitoring of the progress of treatment, and in the context of a screening assay, for the identification of an anti-SCI therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of SCI. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, plasma, serum, peripheral blood, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., an SCI treatment) on a patient. In yet another embodiment, a transcription rate, mRNA level, translation rate, protein level, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, etc. A "suitable control" can be a profile or pattern of levels of one or more biomarkers of the present invention that correlates to SCI, to which a patient sample can be compared. The patient sample can also be compared to a negative control, i.e., a profile that correlates to not having SCI.

The term "isolated" designates a biological material (nucleic acid or protein) that has been removed from its original environment (the environment in which it is naturally present). For example, a polynucleotide present in its natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

The term "percent identity" or "percent identical," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.)

Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized. The terms "specifically binds to," "specific for," and related grammatical variants refer to that binding which occurs between such paired species as antibody/antigen, aptamer/target, enzyme/substrate, receptor/agonist and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, in certain embodiments, "specific binding" occurs between a paired species where there is interaction between the two which produces a bound complex having the characteristics of, for example, an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins.

In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. In certain embodiments, the term refers to a molecule (e.g., an aptamer) that binds to a target (e.g., a protein) with at least five-fold greater affinity as compared to any non-targets, e.g., at least 10-, 20-, 50-, or 100-fold greater affinity.

Optional" or "optionally" means that the subsequently described event or circumstance can or cannot occur, and that the description includes instances where the event or circumstance occurs and instances where it does not.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the terms "antibody fragments", "fragment", or "fragment thereof" refer to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. In most embodiments, the terms also refer to fragments that binding an antigen of a target molecule (e.g., neurogranin) and can be referred to as "antigen-binding fragments."

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence.

The humanized antibody can also comprise at least a portion of an immunoglobulin constant region (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

II. Neurogranin Aptamers

The present invention relates to polynucleotide aptamers that specifically bind to neurogranin. In certain embodiments, the aptamers are used for neurogranin detection. The sequence of the polynucleotide aptamers of the invention are disclosed herein, and further aptamer embodiments may be selected by any method known in the art. In one embodiment, aptamers may be selected by an iterative selection process such as Systemic Evolution of Ligands by Exponential Enrichment (SELEX). In this type of process, a random pool of oligonucleotides (e.g., about $10^5$ to about $10^{15}$ random oligonucleotides) is exposed to a target protein and the oligonucleotides that bind to the target are isolated and mutagenized and the process repeated until oligonucleotides that bind with the desired affinity to the target are identified. In another embodiment, aptamers may be selected by starting with the sequences and structural requirements of the aptamers disclosed herein and modifying the sequences to produce other aptamers.

In one embodiment of the invention, the aptamers are directed to a mammalian neurogranin protein. In further embodiments, the aptamers may be directed to human, mouse or rat neurogranin. In another embodiment, the aptamers are directed to human, mouse and rat neurogranin. In particular embodiments, the aptamers may bind neurogranin with a $K_d$ of less than about 1000 nM, e.g., less than about 500, 200, 100, 50, or 20 nM. The aptamers may be directed to any isoform or post-translationally modified form of neurogranin or any combination of isoforms, post-translationally modified forms and the like.

The length of the aptamers of the invention is not limited, but typical aptamers have a length of about 10 to about 100 nucleotides, e.g., about 20 to about 80 nucleotides, about 30 to about 50 nucleotides, or about 40 nucleotides. In certain embodiments, the aptamer may have additional nucleotides attached to the 5'- and/or 3' end. The additional nucleotides may be, e.g., part of primer sequences, restriction endonuclease sequences, or vector sequences useful for producing the aptamer.

The polynucleotide aptamers of the present invention may be comprised of, ribonucleotides only (RNA aptamers), deoxyribonucleotides only (DNA aptamers), or a combination of ribonucleotides and deoxyribonucleotides. The nucleotides may be naturally occurring nucleotides (e.g., ATP, TTP, GTP, CTP, UTP) or modified nucleotides. Modified nucleotides refers to nucleotides comprising bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific examples include 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methyl aminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methyl carbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. Modified nucleotides include labeled nucleotides such as radioactively, enzymatically, or chromogenically labeled nucleotides.

In one embodiment of the invention, the aptamer is a RNA aptamer and comprises a nucleotide sequence that is identical to any of SEQ ID NOS:4-6. In another embodiment, the RNA aptamer consists of a nucleotide sequence that is identical to any of SEQ ID NOS:4-6. In a further embodiment, the RNA aptamer comprises a nucleotide sequence that is at least 70% identical, e.g., at least 75%, 80%, 85%, 90%, 91%, 92%, 93%, 94%, 95%, 96%, 97%, 98%, or 99% identical to any of SEQ ID NOS:4-6. In another embodiment, the aptamer consists of a nucleotide sequence that is at least 70% identical, e.g., at least 75%, 80%, 85%, 90%, 91%, 92%, 93%, 94%, 95%, 96%, 97%, 98%, or 99% identical to any of SEQ ID NOS:4-6. In a different embodiment, the aptamer comprises a nucleotide sequence that is identical to a fragment of any of SEQ ID NOS:4-6 of at least 10 contiguous nucleotides, e.g., at least about 15, 20, 25, 30, or 35 contiguous nucleotides. In a further embodiment, the aptamer comprises a nucleotide sequence that is at least 70% identical, e.g., at least 75%, 80%, 85%, 90%, 91%, 92%, 93%, 94%, 95%; 96%, 97%, 98%, or 99% identical to a fragment of any of SEQ ID NOS:4-6 of at least contiguous 10 nucleotides, e.g., at least about 15, 20, 25, 30, or 35 contiguous nucleotides. In one embodiment, one or more ribonucleotides in the RNA aptamers described above are substituted by a deoxyribonucleotide. In another embodiment, the fragments and/or analogs of the aptamers of SEQ ID NOS:4-6 have a substantially similar binding and/or inhibitory activity as one or more of the aptamers of SEQ ID NOS:4-6. "Substantially similar," as used herein, refers to a binding and/or an inhibitory activity on one or more neurogranin functions that is at least about 20% of the binding and/or inhibitory activity of one or more of the aptamers of SEQ ID NOS:4-6.

Changes to the aptamer sequences, such as SEQ ID NOS:4-6, may be made based on structural requirements for binding of the aptamers to neurogranin. The structural requirements may be readily determined by one of skill in the art by analyzing common sequences between the disclosed aptamers and/or by mutagenizing the disclosed aptamers and measuring neurogranin binding affinity. For example, each of NRGN-A1, NRGN-A2, NRGN-A3, NRGN-A4 and NRGN-A5 comprise 2T-rich motifs which are separated by CC, suggesting that this sequence is important for binding activity.

The aptamer may by synthesized by any method known to those of skill in the art. In one embodiment, aptamers may be produced by chemical synthesis of oligonucleotides and/or ligation of shorter oligonucleotides. Another embodiment of the present invention relates to polynucleotides encoding the aptamers of the invention. The polynucleotides may be used to express the aptamers, e.g., by in vitro transcription, polymerase chain reaction amplification, or cellular expression. The polynucleotide may be DNA and/or RNA and may be single-stranded or double-stranded. In one embodiment, the polynucleotide is a vector which may be used to express the aptamer. The vector may be, e.g., a plasmid vector or a viral vector and may be suited for use in any type of cell, such as mammalian, insect, plant, fungal, or bacterial cells. The vector may comprise one or more regulatory elements necessary for expressing the aptamers, e.g., a promoter, enhancer, transcription control elements, etc. One embodiment of the invention relates to a cell comprising a polynucleotide encoding the aptamers of the invention. In another embodiment, the invention relates to a cell comprising the aptamers of the invention. The cell may be any type of cell, e.g., mammalian, insect, plant, fungal, or bacterial cells.

One aspect of the present invention relates to the use of the aptamers of the invention for diagnostic purposes. The aptamers can be used as binding agents in assays for measuring the level of neurogranin in a subject. Such measurements can be used to determine if neurogranin levels are abnormal. Such measurements can further be used to diagnose a disease or disorder associated with neurogranin, e.g., associated with neurogranin overexpression or underexpression. In other embodiments, the aptamers can be used in neurogranin receptor competitive binding assays to measure the abundance of neurogranin receptors and/or the binding affinity and specificity of neurogranin for the receptors. The aptamers can also be used for in vivo imaging or histological analysis. Numerous suitable binding assays are well known to those of skill in the art. Diagnostic assays can be carried out in vitro on isolated cells or cell lines for research purposes. Diagnostic assays can also be carried out on samples from a subject (e.g., tissue samples (biopsies, aspirates, scrapings, etc.) or body fluid samples (blood, plasma, serum, saliva, urine, cerebrospinal fluid, etc.)) or carried out in vivo. The aptamers can be labeled using methods and labels known in the art including, but not limited to, fluorescent, luminescent, phosphorescent, radioactive, and/or colorimetric compounds.

In one aspect, the invention relates to a method of measuring the level of neurogranin in a subject, comprising the step of using the polynucleotide aptamer of the invention to bind neurogranin. In another aspect, the invention relates to a method of diagnosing a disease or disorder associated with neurogranin in a subject, comprising the step of measuring the level of neurogranin in the subject using the polynucleotide aptamer of the invention. The level of neurogranin can then be correlated with the presence or absence of a disease or disorder associated with neurogranin.

For each of the methods described above, the methods may be carried out using a single aptamer targeted to neurogranin. In another embodiment, the methods may be carried out using two or more different aptamers targeted to neurogranin, e.g., three, four, five, or six different aptamers.

III. Neurogranin Antibodies

In one aspect, the present invention provides antibodies to neurogranin that are useful for diagnostic or screening purposes. In certain embodiments, the antibodies described herein are isolated. In certain embodiments, the antibodies described herein are substantially pure.

In some embodiments the antibodies are monoclonal antibodies. In certain embodiments, the antibodies are chimeric, humanized, or human antibodies. The invention further provides bispecific antibodies. In certain embodiments, the antibodies are antibody fragments, such as Fab fragments.

In particular embodiments, the present invention provides isolated antibodies against neurogranin. In a specific embodiment, the antibodies are specific for SEQ ID NO: 11. In other embodiments, the antibodies specifically bind amino acids 55-78 of SEQ ID NO: 11. The antibody, or antibody fragment thereof, can be any monoclonal or polyclonal antibody that specifically recognizes neurogranin. In some embodiments, the present invention provides monoclonal antibodies, or fragments thereof, that specifically bind to neurogranin. In some embodiments, the monoclonal antibodies, or fragments thereof, are chimeric or humanized antibodies that specifically bind to neurogranin or an epitope or antigenic determinant thereof.

The antibodies against neurogranin find use in the experimental and diagnostic methods described herein. In certain embodiments, the antibodies of the present invention are used to detect the expression of a neurogranin protein in biological samples such as, for example, a tissue, blood, plasma, serum, cerebrospinal fluid sample and the like. Tissue biopsies can be sectioned and neurogranin protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of neurogranin, for example, on cells, in cell lysates, or in other protein samples.

Polyclonal antibodies can be prepared by any known method. Polyclonal antibodies can be raised by immunizing an animal (e.g., a rabbit, rat, mouse, donkey, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against neurogranin is a humanized antibody. Humanized antibodies are antibodies that contain minimal sequences from non-human (e.g., murine) antibodies within the variable regions. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments of the invention, it may be desirable to use an antibody fragment, rather than an intact antibody. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention further provides kits and articles of manufacture comprising one or more antibodies. In certain embodiments, the kits comprise at least two antibodies. In certain embodiments, the kits comprise at least one antibody that specifically binds a neurogranin protein.

IV. Detection of Neurogranin and Other Biomarkers

A. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer, hybrids or combinations of the foregoing, and the like. In a specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein. In another embodiment, the mass spectrometric technique is multiple reaction monitoring (MRM) or quantitative MRM.

In an alternative embodiment, the mass spectrometric technique comprises surface enhanced laser desorption and ionization or "SELDI," as described, for example, in U.S. Pat. No. 6,225,047 and No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In other embodiments, the biomarkers of the present invention can be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds all neurogranin and/or one or more of its breakdown products might be used. Aptamers are nucleic acid-based molecules that bind specific ligands. Methods for making aptamers with a particular binding specificity are known as detailed in U.S. Pat. No. 5,475,096; No. 5,670,637; No. 5,696,249; No. 5,270,163; No. 5,707,796; No. 5,595,877; No. 5,660,985; No. 5,567,588; No. 5,683,867; No. 5,637,459; and No. 6,011,020.

C. Detection by Electrochemiluminescent Assay

In several embodiments, the biomarker biomarkers of the present invention may be detected by means of an electrochemiluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; No. 7,491,540; No. 7,288,410; No. 7,036,946; No. 7,052,861; No. 6,977,722; No. 6,919,173; No. 6,673,533; No. 6,413,783; No. 6,362,011; No. 6,319,670; No. 6,207,369; No. 6,140,045; No. 6,090,545; and No. 5,866,434. See also U.S. Patent Application Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described that in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

V. Kits for the Detection of Neurogranin and Other Brain Injury Biomarkers

In another aspect, the present invention provides kits for qualifying brain injury status, which kits are used to detect neurogranin and other biomarkers. In a specific embodiment, the kit is provided as an ELISA kit comprising antibodies to neurogranin. In other embodiments, a kit can comprise antibodies to one or more of ASTN1, BAI3, CNDP1, ERMIN, GFAP, GRM3, KLH32, MAGE2, NRG3, OMG, SLC39A12, RTN1, and MT3.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

In other embodiments, the kit for qualifying brain injury status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Development of Neurogranin Assay

The Identification of Human NRGN Specific Aptamers.
Systematic Evolution of Ligands by EXponential enrichment (SELEX) procedure was used to identify the human NRGN specific aptamers. Briefly, the specific aptamer was selected from a pool of single strand RNA by filter immobilization. The RNA-NRGN target complex can bind to nitrocellulose filter, and free RNA went through filtration. The specific aptamer was recovered from the filter and PCR amplified. After several round of selection, the specific aptamer with highest affinity with NRGN was enriched and sequencing identified.

Prepare the Library for Selection.
Single strand DNA oligo pool was chemically synthesized. The DNA oligo has 40mer random central core, which flanked by 2 constant sequences, and the library can be amplified by a pair of primers which target the 5' and 3' conserve ends of the library. The sequence of the library is 5'-TCTCGGATCCTCAGCGAGTCGTCTG (N40) CCG-CATCGTCCTCCCTA-3' (SEQ ID NO:1).

Generating RNA Library.
The single strand DNA library first was annealed with Sel2 5' primer, the sequence is 5'-GGGGGAAT-TCTAATACGACTCACTATAGGGAGGACGATGCGG-3' (SEQ ID NO:2), which contains a T7 promoter for in vitro transcription. The gap was filled in by Klenow reaction, which was performed at 37° C. for 1.5 hours. The reaction was purified by phenol:chloroform:isoamyl (25:24:1) and chloroform:isoamyl (24:1) extraction once each and further concentrated with Centricon 30 at 4° C. TE buffer, pH7.4 was used to wash the reaction twice while concentration process. The final OD260 was measured and concentration was determined.

The above annealed oligo pool was used to generate an RNA library for SELEX by in vitro transcription, using the DuraScribe® T7 Transcription Kits (Epicentre, DS010910), following the manufacture's reaction condition. 2'-Fluorine-CTP (2'-F-dCTP) and 2'-Fluorine-UTP (2'-F-dUTP) were used to replace CTP and UTP in the transcription reaction, the final DuraScript® RNA (2'-fluorine-modified RNA) is completely resistant to RNase A. After in vitro transcription, DNase I was used to treat the reaction and the RNA was extracted with phenol:chloroform:isoamyl (25:24:1) and chloroform once each, followed by concentrate and desalt with Centricon 30 at 4° C.

The RNA was further purified by denatured PAGE (12%, 7M Urea) gel purification. The RNA band was cut from the PAGE gel, RNA was eluted in 2 ml TE buffer overnight at 4° C. The pure RNA was concentrate again using Centricon 30, and concentration of RNA was determined using conventional method.

Nitrocellulose Filter Pre-Clear.
A 13 mm Swin-Lok Filter holder (Whatman) (13-mm diameter), 0.45 um pore size HAWP nitrocellulose disk filters (Millipore) was assembled. The filter was pre-wet with 1 ml washing buffer, which contains 20 mM Hepes pH7.4, 50 mM NaCl and 2 mM $CaCl_2$. 500 pmol RNA was diluted in 100 ul 1× binding buffer (the formula is the same as washing buffer except 0.1% BSA was added), and applied into the reservoir of the filter holder. The filter holder was sealed into a 50 ml conical tube and incubated at 37° C. for 30 minutes. After incubation, the RNA was recovered by pass through the filter unite using 1 ml syringe, and 100 µl of 1× binding buffer was used to wash once. The RNA passed through the filter was collected; total pre-cleared RNA was about 180 µl.

Binding Reaction.
The binding reaction was assembled by adding 50 pmol human NRGN protein into the pre-cleared RNA, the molecular ratio of RNA:protein was about 10:1. The total volume was brought to 200 µl in 1× binding buffer. The reaction was incubated at 37° C. for 15 minutes. A new filter holder was assembled and pre-wet as above, the binding reaction to the filter was applied, a 5 ml syringe was used to push the binding sample through, and the filter was washed with 5 ml wash buffer.

Recover the Selected RNA.
The filter holder was disassembled, and the filter was transferred into a 1.5 ml centrifuge tube which contained 600 ul phenol:chloroform:isoamyl (25:24:1). The tube was vortexed vigorously for approximately 1 min, then incubated at RT for 30 minutes. Two hundred microliters of $H_2O$ was added and vortexed again, then spun at 14,000 rpm for 10 minutes. The supernatant, which contained the recovered RNA, was extracted with 400 ul chloroform once, then precipitated by adding 500 µl ethanol, 20 µl 3M NaAcetate (pH 5.2) and 3 µl Glycogen blue (Ambion, 5 mg/ml), and then incubated at −80° C. overnight. The RNA was recovered by centrifugation at 14000 rpm for 20 minutes at 4° C., then washed with 1 ml 75% ethanol once, followed by centrifugation and air drying of the RNA. The dried RNA pellet was dissolved into 20 µl $H_2O$.

Amplify the Selected RNA by RT-PCR.
Five microliters of recovered RNA was used to synthesize the first strand of DNA. Two micromolar of primer Sel2 3' was added into the reaction. The sequence of Sel2 3' primer is: 5'-TCT CGG ATC CTC AGC GAG TCG TC-3' (SEQ ID NO:3). Reverse Transcriptase from Roche (Cat. No. 10 109 118 001) was used in the reaction, the conditions were as recommended by the manufacture.

The PCR reaction was assembled as follows: 5 µl first stand DNA (from above step), 3 µl of each 10 µM primers (Sel2 3' from above step and Sel2 5' from above step), 39 µl $H_2O$ and 50 µl 2× TopTaq Master Mix (Qiagen). A total of 8 reactions (800 ul) were performed. The PCR cycle condition was as follow: 94° C./5'→(94° C./30"→55° C./30"→72° C./30")×20 cycles→4° C. The PCR product was confirmed by 3% agarose gel electrophoresis, and the rest of PCR product were desalted and concentrated using a Centricon 30 at 4° C. The concentration of PCR product was determined by measuring OD/260 nm.

Repeat the Selection.
One microgram of concentrated PCR product was used to generate RNA for the next round selection, the protocols for in vitro transcription were followed as described above. A total of 10 rounds of selection were performed.

After 10 rounds of selection, another 3 rounds of selection were performed using high-salt binding buffer to increase the selection stringency. The formula for 1× binding buffer F and washing buffer F is the same as the buffers described above, except that the concentration of NaCl was increased to 150 mM. The other detailed procedure is the same as that described above.

The final PCR product after 13 rounds of selection was cloned into pGEM-T Easy vector (Promega), the enriched aptamers were identified by DNA sequencing. The clones containing the full primers and 40mer insert were aligned using ClustalW2 at EMBL-EBI website.

The Identified Human NRGN Specific Aptamers.

Six clones were chosen for sequencing; the quality of all of the sequences was very high. After the DNA alignment analysis, 5 out of the 6 clones were almost identical, except that NRGN-A4 had one nucleotide difference (underlined). The less similar one, NRGN-A6, comparing with the other well aligned 5 clones, showed that all of them have 2 T-rich motifs, which are separated by CC/CA (boxed). NRGN-A1 and NRGN-A6 were selected as targets for validation. The following showed the alignment of the aptamers:

```
                                                       (SEQ ID NO: 4)
NRGN-A1  TCTAACGCCTCCCGTATGTTTTCGT---TTTT-CCATTG---CGGAT 40

(SEQ ID NO: 4)
NRGN-A2  TCTAACGCCTCCCGTATGTTTTCGT---TTTT-CCATTG---CGGAT 40

(SEQ ID NO: 4)
NRGN-A3  TCTAACGCCTCCCGTATGTTTTCGT---TTTT-CCATTG---CGGAT 40

(SEQ ID NO: 4)
NRGN-A5  TCTAACGCCTCCCGTATGTTTTCGT---TTTT-CCATTG---CGGAT 40

(SEQ ID NO: 5)
NRGN-A4  TCTAACGCCTCCCGCATGTTTTCGT---TTTT-CCATTG---CGGAT 40

(SEQ ID NO: 6)
NRGN-A6  -TTTTCATTTTC---ATTTTTTTCCAAATCGATCCGCCGGACCTTAT 43
```

Validation of the Aptamer-NRGN Interaction.

NRGN-A1 and NRGN-A6 RNA were chemically synthesized based on the sequences identified; adding a biotin linker to the RNA 3' end. Two different strategies were used to test NRGN aptamer and NRGN recombinant protein interaction. The details are as described below.

Using Dot Blot to Detect the RNA Protein Complex on Nitrocellulose.

Based on the same mechanism that was used in SELEX procedure, RNA-protein complex can be retained on nitrocellulose membrane, a dot blot was used to detect the biotin labeled RNA aptamer. First, a 2-fold series dilution of His-NRGN recombinant protein was made, the amount of protein range from 10 pmol to 0; and then each sample was mixed with 1 pmol of NRGN aptamer RNA. The volume of final binding reaction was kept at 20 µl in 1× binding buffer F, the reactions were incubated at 37° C. for 15 min.

Meanwhile, the dot blot apparatus (Bio-Rad, #170-6545) was setup. The nitrocellulose membrane was cut and shaken in 1× washing buffer F for 30 min prior to use. The nitrocellulose membrane was put on top of pre-wet Whatman paper and placed on the bottom of the apparatus, then the vacuum was assembled and hooked up. The membrane was washed with 100 ul 1× washing buffer F per well once, then the binding reaction was applied. After the reactions were passed through, the membrane was washed with 200 ul 1× washing buffer F once, and then drained by vacuuming. The membrane was then UV-crosslinked (Bio-Rad, #165-5031).

The Chemiluminescent Nucleic Acid Detection Module (Pierce, #89880) was used to detect the Biotin labeled RNA aptamer retained on nitrocellulose, following the manufacturer's instruction. Briefly, the membrane was incubated with streptavidin-HRP conjugate, and detected with the chemiluminescent substrate of HRP.

As a result, both NRGN aptamers NRGN-A1 and A6 bound to NRGN protein, the minimum amount of protein needed for detection using this method was 1.25 pmol and 0.63 pmol respectfully. When the same molar of human albumin was used as control, no signal could be detected, despite the amount of albumin used. This result indicated that both of these 2 aptamers bind to His-NRGN protein specifically. See FIG. 1.

Pull-Down Assay.

Biotin labeled aptamers were immobilized on streptavidin particles and a pull-down assay was performed. Aptamers were diluted to 1 pmol/µl in TEN100 buffer (10 mM Tris-HCl, pH7.5, 1 mM EDTA, 100 mM NaCl), heated at 65° C. for 5', then left at RT for 20 minutes to let the RNA fold into its natural conformation. Streptavidin magnetic particles (Roche, 11641778001) were washed 3 times with twice volume of TEN100 buffer, then the aptamer samples were added and incubated at RT for 30 minute with rotation. After incubation, the particles were washed with TEN100 buffer 3 times, and then equilibrated with 1× binding buffer F once. Different amounts of NRGN protein (0-2 nmol) were diluted in 1× binding buffer and added into the aptamer immobilized magnetic particles, then incubated at 37° C. for 15 minutes.

Figure 2:
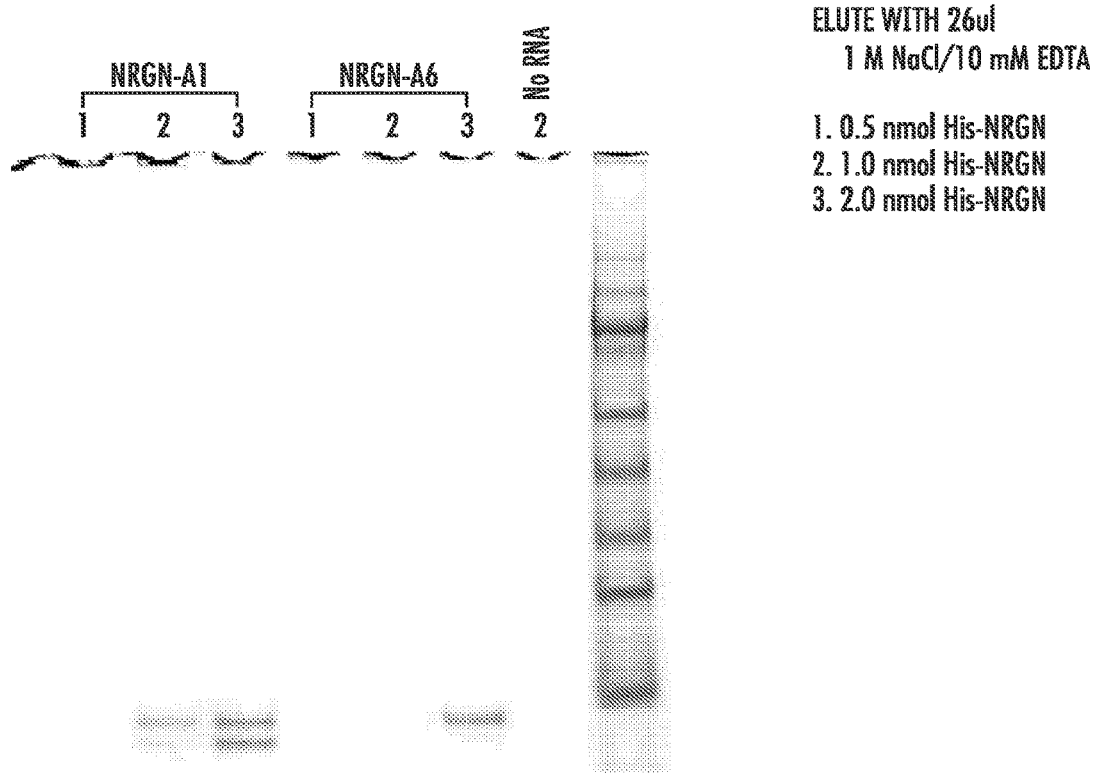
FIG. 2 shows the results of a pull-down assay using the neurogranin aptamers.

After binding incubation, the particles were washed twice with TEN100 buffer. The aptamers protein complex was dissociated by incubating in 26 µl elution buffer (1M NaCl, 10 mM EDTA) at room temperature for 10 min. The eluted protein was subjected to SDS-PAGE, and the protein bands were visualized by Coomassie staining. The human albumin protein was used as negative control. A typical stained gel is shown in FIG. 2.

Both of the dot blot and pull-down assays showed that the aptamers specifically bind to human NRGN recombinant protein.

Development of a Neurogranin Multiple Reaction Monitoring (MRM) Assay.

A neurogranin signature peptide was developed for a mass spectroscopy quantitative MRM assay. The peptide sequence and transitions are shown in the table below. Labeled GPGPGGPGGAGVAR (SEQ ID NO:7) was spiked in the samples to make standard curve to measure the concentration of signature peptide GPGPGGPGGAGVAR (SEQ ID NO:7). Peptide KGPGPGGPGGAGVAR (SEQ ID NO:8) is also monitored to make sure there is no miscleavage in tryptic digestion.

TABLE 8

Neurogranin Peptide Sequences

| Precursor Q1 | Transitions Q3 | Peptide ID |
|---|---|---|
| 553.79 | 366.18 | GPGPGGPGGAGVAR (SEQ ID NO: 7) |
| 553.79 | 423.2 | GPGPGGPGGAGVAR (SEQ ID NO: 7) |
| 553.79 | 684.38 | GPGPGGPGGAGVAR (SEQ ID NO: 7) |
| 553.79 | 741.4 | GPGPGGPGGAGVAR (SEQ ID NO: 7) |
| 553.79 | 798.42 | GPGPGGPGGAGVAR (SEQ ID NO: 7) |
| 553.79 | 895.47 | GPGPGGPGGAGVAR (SEQ ID NO: 7) |
| 553.79 | 952.49 | GPGPGGPGGAGVAR (SEQ ID NO: 7) |
| 558.792 | 366.18 | Labeled GPGPGGPGGAGVAR (SEQ ID NO: 7) |
| 558.792 | 423.2 | Labeled GPGPGGPGGAGVAR (SEQ ID NO: 7) |
| 558.792 | 694.39 | Labeled GPGPGGPGGAGVAR (SEQ ID NO: 7) |
| 558.792 | 751.41 | Labeled GPGPGGPGGAGVAR (SEQ ID NO: 7) |
| 558.792 | 808.43 | Labeled GPGPGGPGGAGVAR (SEQ ID NO: 7) |
| 558.792 | 905.48 | Labeled GPGPGGPGGAGVAR (SEQ ID NO: 7) |
| 617.846 | 684.38 | KGPGPGGPGGAGVAR (SEQ ID NO: 8) |
| 617.846 | 741.4 | KGPGPGGPGGAGVAR (SEQ ID NO: 8) |
| 617.846 | 798.42 | KGPGPGGPGGAGVAR (SEQ ID NO: 8) |
| 617.846 | 950.5 | KGPGPGGPGGAGVAR (SEQ ID NO: 8) |
| 617.846 | 962.5 | KGPGPGGPGGAGVAR (SEQ ID NO: 8) |

Figure 3:
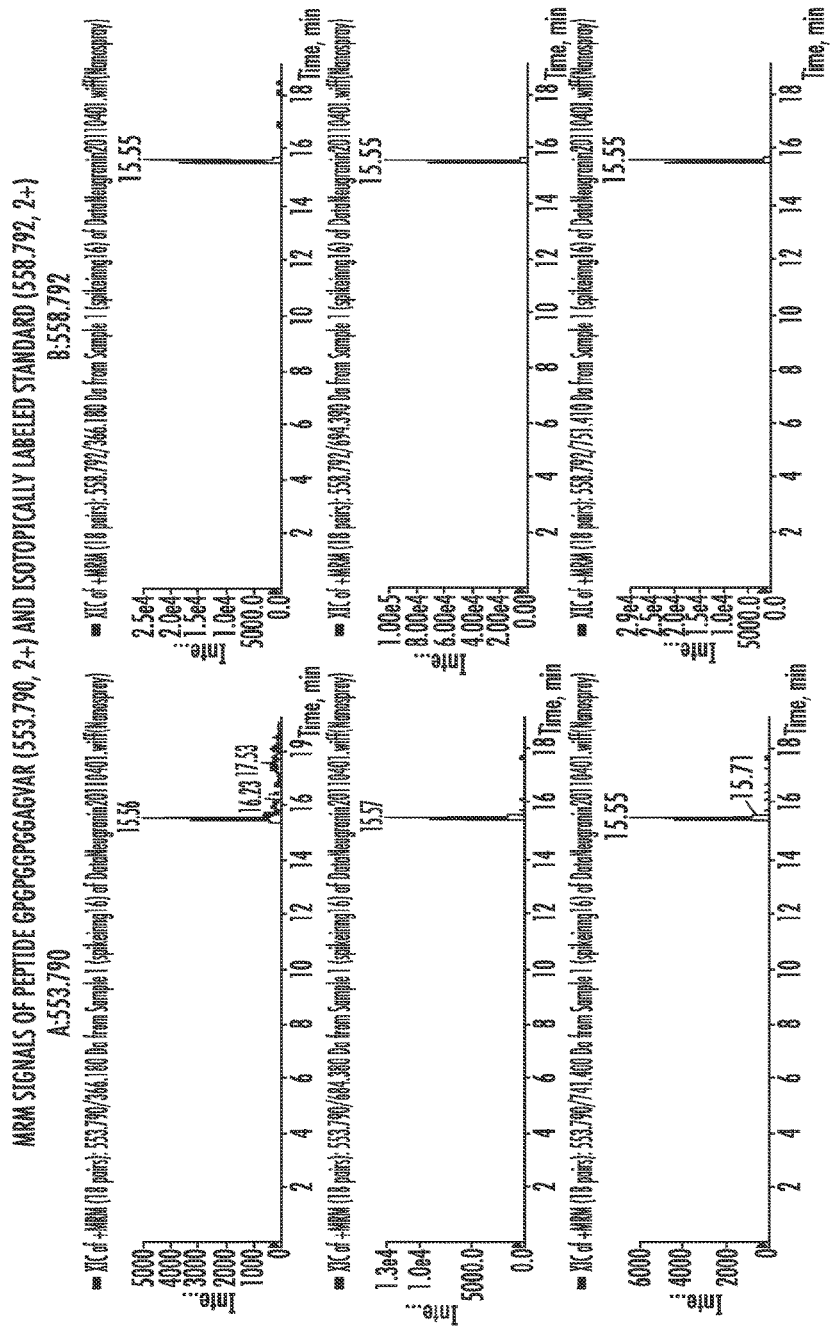
FIG. 3 displays the signals of neurogranin signature peptide and labeled standard peptide using an ABI Sciex Qtrap 4000 triple quadrapole mass spectrometer.

The signals of neurogranin signature peptide and labeled standard peptide using an ABI Sciex Qtrap 4000 triple quadrapole mass spectrometer are shown in FIG. 3.

His-NRGN Recombinant Protein Production.

Figure 4:
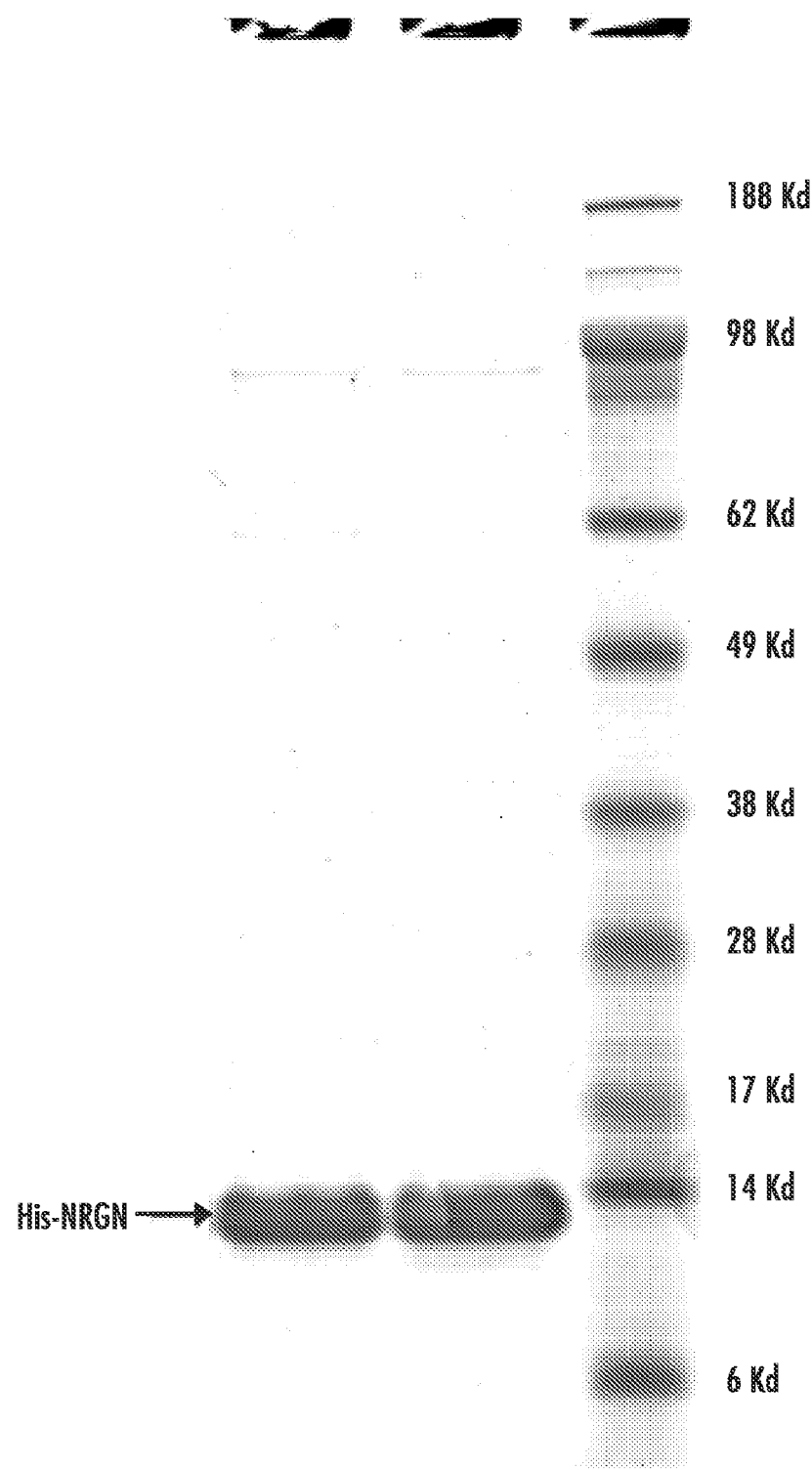
FIG. 4 shows His-NRGN on PAGE gel after Coomassie staining. The predicted molecular weight of His-NRGN is 8.5 Kd.

Human NRGN cDNA clone was purchased from Origene (Cat. No. RC201209). The coding sequence was cloned into destination vector (Origene, pEX-N-His, Cat. No. PS100030) by restriction enzymes (SgfI+Mlu I) fragment swapping to generate pEX-N-His-NRGN expression plasmid. The coding sequence and reading frame were confirmed by DNA sequencing.

pEX-N-His-NRGN plasmid was transformed into Rosetta 2 (DE3) competent cells (Novagen #71397) according to manufacturer's instruction. The bacteria were cultured in the Overnight Express Instant TB Medium (Novagen #71491) at 37° C. for 16-18 hours, then harvested and suspended in TEN buffer (50 mM Tris, pH8.0, 0.5 mM EDTA and 0.5 M NaCl). The bacteria were lysed by adding 1% NP-40, 25 mg lysozyme and complete proteinase inhibitors (Roche), sitting on ice for 30 minutes, then freeze-thaw one time. The lysate was cleared by centrifugation, then Ni-NTA agarose beads (Qiagen) were added into the supernatant, and rotated at 4° C. for 1 hour. The beads were washed 3 times with washing buffer (20 mM Imidazole, 20 mM KCl and 0.5 M NaCl). The recombinant protein was eluted off the beads by rotating the beads in the elution buffer (100 mM Imidazole, 20 mM $K_3PO_4$ and 167 mM NaCl) at 4° C. for 10 minutes. The eluted protein was dialyzed against 3 L PBS overnight, the protein concentration was determined by conventional protein assay. FIG. 4 shows the typical His-NRGN on PAGE gel after Coomassie staining; the predicted molecular weight of His-NRGN is 8.5 Kd.

Development of a Neurogranin Monoclonal.

Figure 5:
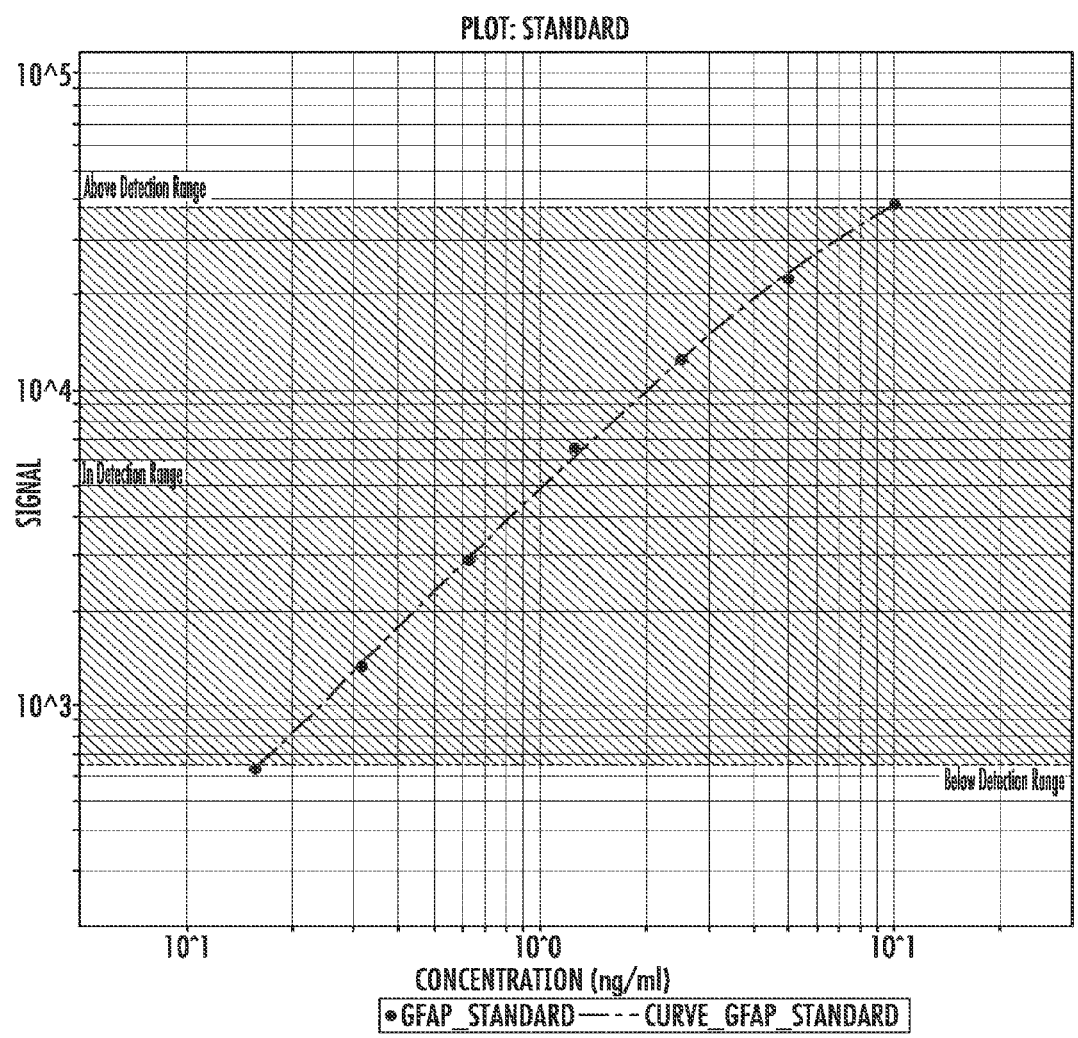
FIG. 5 shows the standard curve of the direct ELISA for recombinant NRGN using mouse monoclonal antibody 30.5.2 (ATCC Deposit Designation PTA-123496). The concentration range is 0.002-10 ng/ml.

Recombinant neurogranin described above was used to immunize mice for monoclonal antibody production at Johns Hopkins. Thirty clones were screened and clone 30.5.2 (ATCC Deposit Designation PTA-123496) was identified that bound neurogranin at high dilution in a direct ELISA shown in FIG. 5.

Development of a Sandwich ELISA for Neurogranin.

Figure 6:
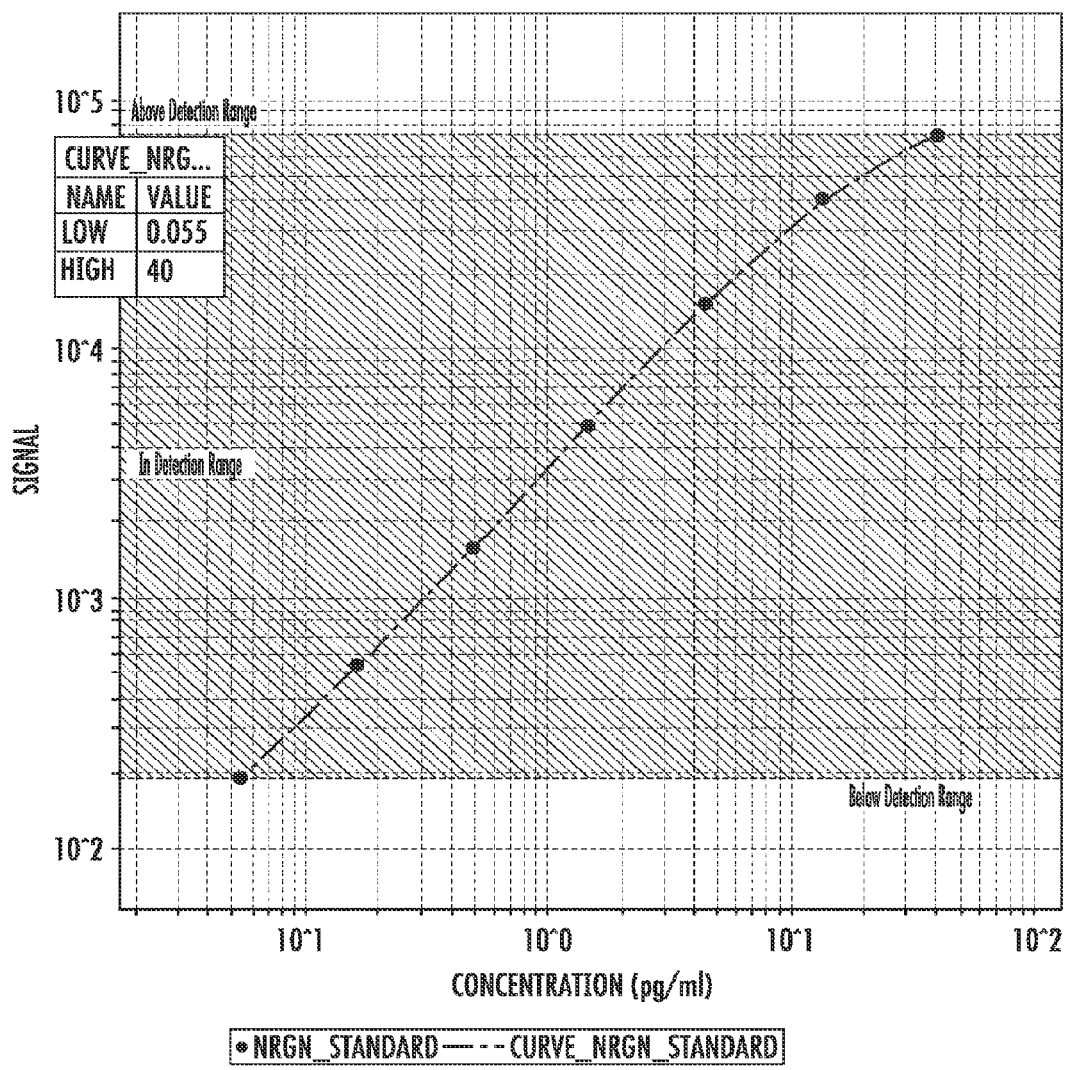
FIG. 6 shows the standard curve of the direct ELISA for recombinant NRGN using an anti-human monoclonal antibody to neurogranin. The concentration range is 75 ng/ml.
Figure 7:
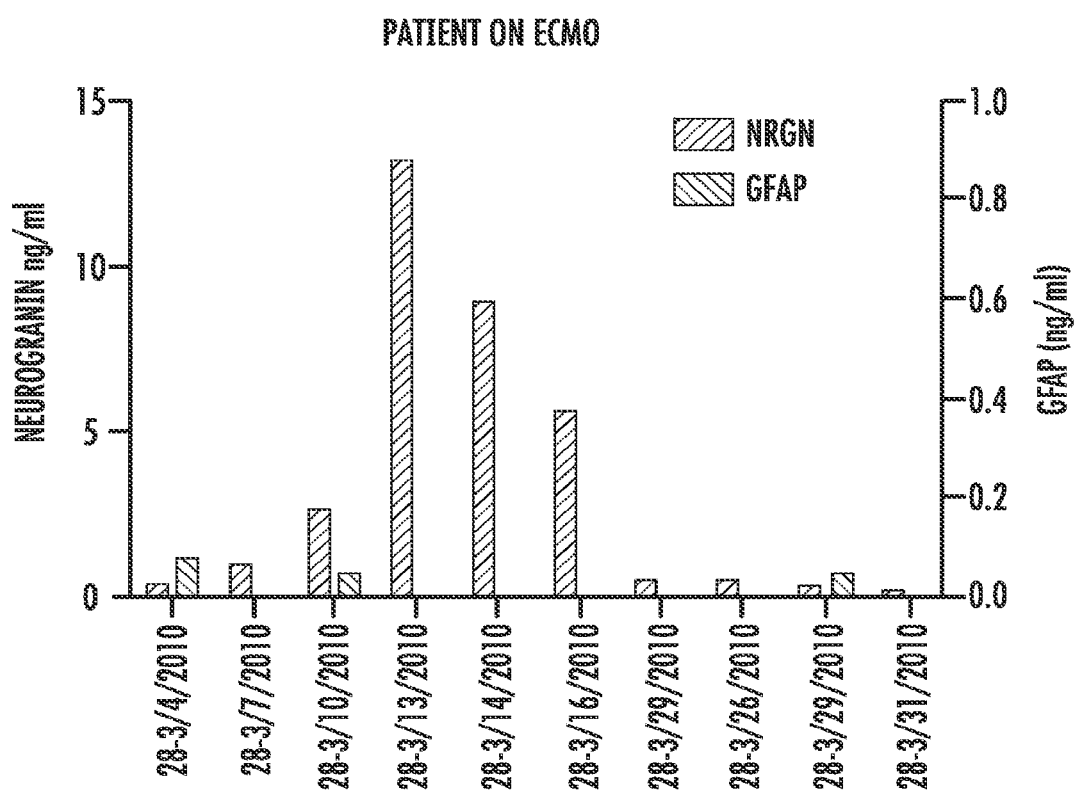
FIG. 7 shows neurogranin and GFAP levels from patients undergoing cardiopulmonary bypass for surgical repair of congenital heart disease.

A Neurogranin anti-Human monoclonal antibody (Johns Hopkins) at concentration of 75 ng/well was used as a capture antibody and a rabbit polyclonal to neurogranin (Johns Hopkins) at a concentration of 0.5 μg/ml was used as detection. SULFO-TAG anti rabbit antibody (MSD Cat#R32AB-1) at a concentration of 1 μg/ml was used as a labeled reporter at a concentration of 1 μg/ml. GST_NRGN recombinant protein (Johns Hopkins) was used as a standard at a starting concentration of 20 ng/ml then at 1:2 for 7 dilutions in PBS/1% BSA. PBS/1% BSA was used as blank. The standard curve for this assay is shown in FIG. 6.

Neurogranin is Biomarker of Acute Brain Injury.

Figure 8:
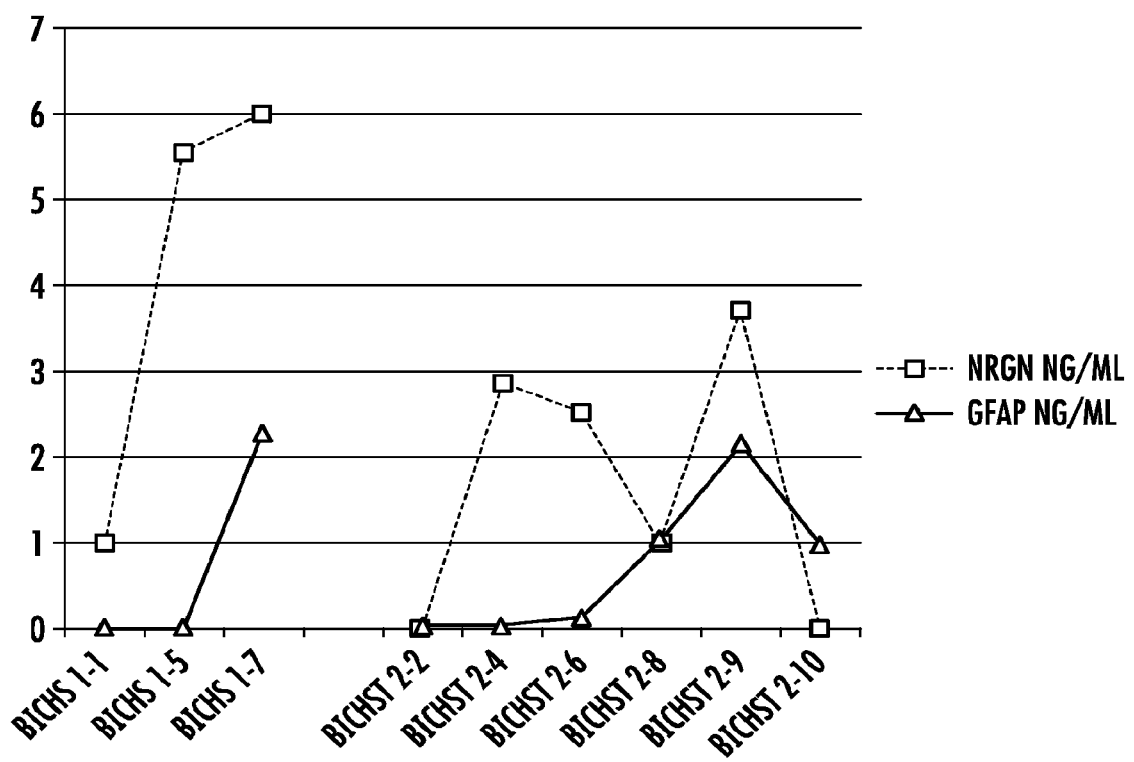
FIG. 8 is a graph showing that neurogranin is a circulating biomarker of acute brain injury and appears earlier in the circulation than glial fibrillary acidic protein, a known circulating biomarker of acute stroke.

Using the neurogranin sandwich assay described above, serum samples from an infant on ECMO support for 27 days for cardio-respiratory failure. The infant had normal daily head ultrasounds and at the time of death was thought to not have brain injury. At autopsy, the brain had multiple cortical infarcts they were not diagnosed by ultrasound. As shown in FIG. 8, GFAP levels were unchanged during the entire course of ECMO support. However, neurogranin levels increased to a peak 15 fold over baseline over 14 days of ECMO support. As neurogranin is a gray matter, neuronal marker it was more sensitive to cortical gray matter injury than GFAP a marker of white matter injury. This provides evidence that neurogranin is a circulating biomarker of acute cortical brain injury and in combination with GFAP is able to discriminate white matter from gray matter injury to the brain.

Example 2: Proteomic Study to Identify Brain Proteins Reveals Elevations of Neurogranin in Children with Sickle Cell Disease Silent cerebral infarct (SCI) is the most common form of neurologic injury in sickle cell disease. It is associated with decreased neurocognitive function, and increased risk for progressive injury, including stroke and new or progressive lesions. SCI is defined as any ischemic lesion visible on multiple T2-weighted magnetic resonance images (MRI) that is not associated with a history or physical exam suggestive of a focal neurologic deficit. To date, a noninvasive, unbiased laboratory test for SCI does not exist, and the ability to identify children with SCD who are at risk for SCI remains limited. Furthermore, the diagnosis of SCI is made with surveillance MRI, which is costly and not done routinely at many institutions. As a result patients are often diagnosed after they have experienced SCI-related impairments.

The identification of plasma brain proteins that can be used as biomarkers of SCI would provide important progress in detection and therapy for children with SCD. Specifically, these potential biomarkers would aid in the identification of children who are at risk for SCI, provide a cost-effective alternative to MRI for early diagnosis, and would allow for monitoring response to treatment. Importantly, biomarkers of SCI would provide insight into the pathological mechanisms involved in the disease. Proteomics methods based on mass spectrometry (MS) provide a platform for the identification, quantification and characterization of these potential biomarkers.

In fact, proteomics has been used for biomarker discovery of brain proteins in a number of disease states, including brain cancer, Alzheimer's disease, traumatic brain injury, and stroke. Mass spectrometry-based approaches have also been used to gain insight into the pathophysiology of SCD. However, very few studies have used plasma proteomics for clinical biomarker discovery in SCD, and none have been published about SCD and subclinical brain injury. Kakhniashvili et al used two-dimensional fluorescence difference gel electrophoresis (2D DIGE) and tandem MS (LC-MS/MS) to evaluate quantitative changes in the red blood cell (RBC) membrane proteome and reported on elevations of proteins involved in repair after oxidative stress. Others have used surface-enhanced laser desorption/ionization time of flight (SELDI-TOF) and Matrix-assisted laser desorption/ionization (MALDI)-TOF MS to evaluate for biomarkers of pulmonary hypertension and acute painful episodes in SCD. The purpose of this study was to use proteomics to identify and validate plasma brain proteins in children with SCD. The present inventors hypothesized that children with SCD and SCI would have circulating plasma brain proteins that could be used as surrogate markers for brain injury, and provide insight into the pathophysiology of the disease.

Materials and Methods

Study Population. The study population was comprised of three groups: children with SCD and SCI, children with SCD and no SCI, and healthy, age-matched controls with no SCD or SCI. Proteomic analysis was done using plasma from seven children with SCD and SCI and six children with SCD but without SCI who were matched for age, hemoglobin and WBC based on current knowledge of risk factors for SCI, as well as on six age-matched African American controls (three with sickle cell trait [SCT]). Cross-sectional plasma samples from a total of 115 children with SCD (64 with SCI and 51 without SCI) and 46 age-matched, African-American controls were used to measure plasma concentrations of identified proteins.

Plasma from children with SCD was randomly selected from those enrolled in the Silent Infarct Transfusion (SIT) Trial (ClinicalTrials.gov identifier NCT00072761). The SIT trial is a multicenter, international clinical study to determine if chronic blood transfusions can effectively prevent the progression of SCI to stroke, in children with SCD aged 5-14 years. Plasma samples and clinical data for healthy controls, without evidence of acute or chronic illness (excluding asthma, behavior/mood disorders, and obesity), were obtained through two separate Institutional Review Board-approved studies.

Sample Preparation.

Baseline steady state peripheral whole blood obtained from children with SCD was collected in EDTA vacutainer tubes (BD, Franklin Lakes, N.J.) at the time of initial screening, and was shipped at room temperature within 24 hours to the SIT Trial Biologic Repository at Johns Hopkins. Upon arrival, samples were and spun at 1500 g for 8 minutes per protocol; plasma was removed and stored at −80° C. until assayed. Steady state peripheral whole blood for the non-SCD controls used for proteomic analysis was collected in EDTA vacutainer tubes, centrifuged at 1500 g (4° C.) for 12 minutes, then aliquoted and stored at −80° C. Plasma samples for the healthy controls used to measure candidate proteins were also collected in EDTA vacutainer tubes and processed according to the SIT Trial protocol.

Hemoglobin Depletion.

Significant hemolysis was observed in the discovery SCD samples. To enrich for low abundance proteins, hemoglobin was depleted from SCD plasma samples (n=15) using nickel-nitrilotriacetic acid (Ni-NTA) beads (Qiagen). Briefly, after Ni-NTA beads were washed with PBS/0.3 M NaCl, 500 µl of plasma was added to 500 µl of 50% nickel beads (250 µl beads in 250 µl PBS/0.3 M NaCl) and subjected to rotation at 4° C. for 20 minutes. Following incubation, the beads were separated from the hemoglobin-depleted sample by centrifugation. Control samples were not subjected to this depletion step.

Protein Quantification.

The Coomassie Blue dye protein assay (BioRad Laboratories, Hercules, Calif., USA) was used for protein quantification.

Protein Enrichment and Purification.

Using the ProteomeLab™ IgY-12 LC10 column kit (Beckman Coulter, Inc., Fullerton, Calif.), second dimension separation and immunoaffinity depletion of 12 abundant plasma proteins (albumin, IgG, fibrinogen, transferrin, IgA, IgM, HDL, apo A-I and apo A-II, haptoglobin, a1-antitrypsin, a1-acid glycoprotein and α2-macroglobulin) was done according to the manufacturer's protocol. Third dimension separation of 400 µg of the enriched proteome, performed on the PF 2D platform (Beckman Coulter, Inc., Fullerton, Calif.), was done using PS-HPRP 2D (4.6×33 mm) columns (Beckman-Coulter, Inc.). Solvent A was 0.1% TFA in water and solvent B was 0.08% TFA in acetonitrile. The gradient was run from 5 to 15% B in 1 min, 15% to 25% in 2 min, 25 to 31% in 2 min, 31 to 41% in 10 min, 41 to 47% in 6 min, 47 to 67% in 4 min, finally up to 100% B in 3 min, held for 1 min, and back to 5% in 1 min at a flow rate of 1 mL/min. The resulting 39 RP-HPLC fractions were obtained using a fraction collector and 96-well plates. The fractionated proteins were dried using a Speedvac system and digested with trypsin (Promega, Madison, Wis.) for MS/MS analysis.

MS Analysis for Protein Identification.

Tandem (LC-MS/MS) experiments were performed on a LTQ-Orbitrap hybrid mass spectrometer (ThermoFisher, San Jose, Calif.) equipped with an on-line nano-HPLC (Agilent technologies, 1200 Series, Wilmington, Del.), as previously described. The LTQ raw data were analyzed using PASS (Integrated Analysis, Bethesda, Md.) with X! Tandem searches (www.thegpm.org; version 2008.12.01) of the non-redundant International Protein Index (IPI) peptide database (human, 3.19). Peptide identifications were accepted if they could be established at greater than 95% probability and contained at least 2 average unique identified spectra, with probability based Mowse scores greater than 35 (p<0.05). A change in charge state of a peptide was not considered a unique identification. The dataset was filtered to 90% sequence identity with CD-HIT.

Proteins, genes, functions and clinical associations were checked and verified using GeneCards (http://www.genecards.org/index.shtml), the National Center for Biotechnology Information (http://www.ncbi.nlm.nih.gov/entrez/query.fcgi?db=PubMed), and Online Mendelian Inheritance in Man (http://www.ncbi.nlm.nih.gov/entrez/query.fcgi?db=OMIM). Protein Atlas, Genenote, GenBank, Unigene, and SwissProt databases were reviewed to identify proteins with increased expression in brain. A composite list of brain proteins was created and used to filter the MS data against to identify brain proteins in children with and without SCD.

Proteins were given a brain tissue specificity score based on their relative expression of transcript in human brain, liver, and 26 other normal human tissues as assessed by available microarray, expressed sequence tags (EST), and serial analysis of gene expression (SAGE) data. Specifically, each protein was scored according to the following criteria: microarray data showing greater than ten-fold increase in expression over baseline, EST and SAGE data showing presence of the protein in less than two other tissues. Proteins received either a score of 1 or 0 for each category, and a maximum score of 3 was assigned if the protein had greater than a ten-fold increase in expression by microarray data, and was found in less than two tissues by EST and SAGE.

Neurogranin was chosen for validation because it showed tissue specificity (brain tissue specificity score=3), had been previously implicated in brain injury, and had the highest total spectral counts of all the brain proteins identified.

Ingenuity Pathway Analysis.

The Ingenuity pathway analysis program (http://www.ingenuity.com) was used to analyze the pathway network of the proteins with abundance changes that were identified through MS. The protein accession numbers were uploaded as an Excel spreadsheet file into the Ingenuity software, which uses the data to navigate the Ingenuity pathways database and extract networks between the proteins. A score better than 2 is usually considered as a valid network.

Development of Immunoassay Protocol.

An electrochemiluminescent sandwich immunoassay was developed for measuring Neurogranin using the MesoScale Discovery platform (MesoScale Discovery, Gaithersburg, Md.). The monoclonal anti-NRGN (neurogranin) antibody described in Example 1 was used for the capture antibody (ab). A polyclonal anti-NRGN antibody (Covance, Berkeley, Calif.) and anti-species Sulfo-Tag (MesoScale Discovery) antibody mixture was used for detection. The standard curve was constructed by serial dilution of purified Neurogranin in 1% bovine serum albumin (SeraCare Life Sciences, Milford, Mass.), from 40 ng/ml to 0.055 ng/ml. Plasma spiked with Neurogranin shows an average of 99% recovery at 10 ng/mL when compared to a standard curve generated with bovine serum albumin. The lower limit of quantification, defined as the lowest dilution with a calculated concentration that does not exceed 20% of the coefficient of variation, was 0.2 ng/mL. The specificity of the assay was tested using GFAP antibody.

Final Neurogranin Assay Protocol.

Standard bind plates (MesoScale Discovery) were coated with 30 µl of monoclonal anti-NRGN antibody pool that was diluted 1:1000 with phosphate-buffered saline (PBS). The plates were incubated overnight and then each well was blocked with 5% BSA/PBS and incubated with shaking (600 rpm) at room temperature for one hour. From a starting concentration of 40 ng/ml, purified Neurogranin was diluted 1:3 with 1% BSA/PBS. Plasma samples were diluted 1:1 using 1% BSA/PBS, then 25 µl of standards and diluted sample were added in duplicate to the plate. After two hours of incubation with shaking, the plates were washed three times with 300 µl/well of PBS with 0.5% Tween-80 (wash buffer) using BioTek (Winooski, Vt.) automatic plate washer. The polyclonal anti-NRGN and anti-species Sulfo-Tag were diluted 1:1000 with 1% BSA/PBS to give a final concentration of 1 µg/mL. Subsequently, 25 µl were added to each well, and each plate was incubated with shaking for one hour before being washed three times. Plates were then read with a Sector Imager 2400 (MesoScale Discovery).

Recombinant Neurogranin Protein Production.

A PCR cloning strategy was used to clone Neurogranin cDNA into bacteria expression vectors to express recombinant proteins. The primers were designed based on human Neurogranin cDNA sequence, SgfI (in forward primer) and MluI (in reverse primer) cutting sites were introduced in to the primers respectively to ensure the correct reading frame and cloning convenience. The sequences for primers are: forward 5'-GAGGCGATCGCCATGGACTGCTGCAC-CGAGAAC-3' (SEQ ID NO:9) and Reverse 5'-GC-GACGCGTCTAGTCTCCGCTGGGGCCGC-3' (SEQ ID NO:10). Human Neurogranin cDNA (Origene, RC201209) was used as template for PCR amplification. The PCR product was digested with SgfI and MluI, gel purified and ligated into pre-digested vectors pEX-N-His-GST (Origene, PS100028) and pEX-N-His (Origene, PS100029) respectively. DH5α competent cells (Invitrogen, 18265017) were used for transformation and plasmid DNA propagation. Positive clones were identified by restriction enzymes digestion analysis and further confirmed by DNA sequencing. The proper plasmids containing correct Neurogranin cDNA were then used to transform Rosetta (Novagen) strain for protein expression. Single positive Rosetta clone was grown in Overnight Express Instant TB media (Novagen, #71491) at 37° C. overnight. Ni-NTA Superflow Columns (Qiagen, #30622) was used to purify His-NRGN protein, Glutathione Spin Column (Pierce, #16104) was used to purify His-GST-NRGN protein; all the purification procedures were followed manufacturer's instructions. The samples of recombinant proteins were subjected to SDS-PAGE and visualized by Coomassie staining; the protein bands were then isolated, digested and confirmed by mass spectrometry analysis.

Monoclonal Antibody Production.

Mouse anti-NRGN monoclonal antibody was produced at The Monoclonal Antibody Core Facility (MACF) at Johns Hopkins University, Department of Neuroscience. Briefly, five 6 weeks old BALB/c female mice (Charles River, Wilmington, Mass.) were immunized with intraperitoneal injection of 100 ug of His-NRGN and boosted on day 21 with using a same route. Then the mice were subcutaneous injection with 50 ug of His-NRGN in Incomplete Freund's Adjuvant twice. Blood was collected 10 days following the third immunization. The sera were tested by direct ELISA using His-GST-NRGN protein as target protein. The mouse with best titer in the ELISA was selected for a final intravenous (iv) boost. On day 89, the mouse was sacrificed and the spleen was removed for the fusion process.

Polyethyleneglycol (MW1500, Sigma) was used to fuse P3x653.Ag8 mouse myeloma cells with spleen cells from the immunized mouse. Fused cells were distributed in 96-well tissue culture plate containing feeder cells harvested from the peritoneum of a normal BALA/c mouse primed intraperitoneally with 0.5 ml Incomplete Freund Adjuvants 4 days earlier. After 10 days of undisturbed culture in selection medium (DMEM containing 20% FCS, Hyclone, supplemented 1×OPI (Sigma), 100 µM hypoxanthine, 0.4 µM aminopterin, and 160 µM thymidine), supernatants were tested with ELISA as described above. Positive colonies were cloned twice by limiting dilution on splenocytes from normal BALA/c mice as feeder cells.

The cloned hybridoma line (30.5.2; (ATCC Deposit Designation PTA-123496)) was grown in DMEM containing 10% defined FCS (Hyclone) supplemented with 1×OPI for 4 to 6 days. Then, hybridoma cells were adapted to growth in serum free media, which would have allowed antibody production in the in vitro system. When cells were in log growth phase, $2 \times 10^7$ cells were inoculated into the in vitro system. The culture supernatant (antibody) was collected every five days.

Statistics.

The differences in clinical characteristics between groups were assessed using two-tailed t-tests with unequal variance. The differences between groups for Neurogranin were compared using the non-parametric Mann-Whitney U test. The Kruskal-Wallis test was used to compare median plasma levels across the three groups: SCD with SCI, SCD without SCI, and healthy controls. Correlations between Neurogranin concentrations and other variables were estimated according to Pearson. In the analyses, a P value less than 0.05 was considered statistically significant. Statistical analyses were conducted using Stata version 11.0 (StataCorp., College Station, Tex.).

Results

Baseline Characteristics of Children with SCD and Controls.

As expected, comparisons of the plasma samples used for proteomic analysis showed that children with SCD (n=15) have significantly lower baseline hb and hematocrit (hct) values as compared to their healthy non-SCD counterparts (n=6) (Table 1).

TABLE 1

Clinical Characteristics of Children with SCD and Healthy, Non-SCD Controls

|  | SCD (n = 15) | Non-SCD (n = 6) |
| --- | --- | --- |
| % SCT (n) | — | 50 (3) |
| % Male (n) | 67 (10) | 50 (3) |
| Age | 9.4 (2.7) | 11.5 (2.1) |
| Retic (%)$^A$ | 9.5 (2.7) | 0.9 (0.3) |
| Hb (g/dL)$^A$ | 8.5 (0.8) | 12.3 (0.9) |
| Hct (%)$^A$ | 23.9 (2) | 37 (2.5) |
| WBC (×10$^9$/L)$^A$ | 14.9 (5.5) | 5.5 (1.4) |
| Plt (×10$^9$/L)$^A$ | 463 (126) | 330 (19) |

Results represent mean ± standard deviation. SCT, sickle cell trait, Retic, reticulocyte; Hb, hemoglobin; Hct, hematocrit; WBC, white blood cell count; Plt, platelet.
$^A$$P < 0.05$ between groups by Student's t-test.

WBC and reticulocyte counts were significantly higher in children with SCD. Table 2 shows the baseline demographic information for SCD children with and without SCI that were used for proteomic analysis (n=7 SCI, 8 non-SCI) and for the quantification of Neurogranin (n=65 SCI, 51 non-SCI). There were no significant differences in baseline hb, WBC, platelet or reticulocyte counts. Patients with SCI had higher levels of total bilirubin as compared to SCD children without SCI.

TABLE 2

Clinical Characteristics of Children with SCD

|  | For Proteomic Analysis (n = 15) | | For Protein Quantification (n = 115) | |
| --- | --- | --- | --- | --- |
|  | SCI (n = 7) | Non-SCI (n = 8) | SCI (n = 65) | Non-SCI (n = 51) |
| % Male (n) | 71 (5) | 63 (5) | 53 (34) | 41 (21) |
| Age | 9.8 (2.4) | 9 (3.1) | 9.8 (3.1) | 8.9 (2.9) |
| Retic (%) | 11 (2.10 | 8.2 (2.6) | 11 (4.8) | 10.6 (3.8) |
| Hb (g/dL) | 8.3 (0.89) | 8.6 (0.7) | 8.3 (1.1) | 8.6 (1.2) |
| Hct (%) | 23.3 (2.3) | 24 (1.8) | 23.6 3.5) | 24.5 (3.6) |
| WBC (×10$^9$/L) | 15.8 (7.5) | 14.1 (3.1) | 12.1 (4.6) | 13.4 (10.1) |
| Plt (×10$^9$/L) | 410 (79) | 510 (145) | 453 (143) | 435 (164) |
| TBili$^A$ | 5.6 (3.4) | 2.7 (0.9) | 3.7 (2.4) | 2.9 (1.6) |

Results represent mean (± standard deviation) (SD). Retic, reticulocyte; Hb, hemoglobin; Hct, hematocrit; WBC, white blood cell count; Plt, platelet; TotBili, total bilirubin.
$^A$$P < 0.05$ between groups by Student's t test.

Characterization of the Plasma Proteome of Children with SCD.

Using three sequential separation steps of Hb removal, immunoaffinity fractionation, and HPLC separation, followed by tandem MS and X! Tandem searches of the IPI peptide database, 752 proteins were identified in the SCI group and an additional 390 proteins were identified in the non-SCI group, totaling 1162 unique proteins circulating in the plasma proteome of children with SCD. An additional 239 proteins were identified in healthy controls (n=639 total proteins in non-SCD children). Thirty percent (343/1162) of the proteins identified in children with SCD were seen in the SCI group and not in the non-SCD group.

Analysis using ingenuity pathway software revealed that the proteins identified in both SCD and normal controls demonstrated significant overrepresentation of a number of biological functions and pathways, including cell-to-cell signaling and cell death, immune cell trafficking, and acute phase response signaling. Neurological disease was ranked amongst the top five diseases in the SCI and normal groups, but not in the non-SCI group. Further analysis revealed that the proteins involved in the SCI group pathways are involved in more specific disease processes that have already been implicated in sickle cell disease, namely ischemia-reperfusion injury, endothelial dysfunction and neuronal injury and death. Furthermore, in children with SCD and SCI the specific conditions related to neurologic disease differed from the normal controls in that proteins associated with tauopathy (microtubule-associated protein tau, glial fibrillary acidic protein) and cerebral amyloid angiopathy (cystatin C, vimentin) were seen in the SCI group only. In addition, while loss of neurites were seen in both the SCI and normal groups, only the SCI group had proteins associated with loss of axons (microtubule-associated protein tau), suggesting neuronal injury in addition to cell death.

Identification of Brain Proteins.

The MS data was filtered against a list of proteins with increased protein expression in brain to produce a composite list of brain proteins that are found in children with SCD. Using this methodology, a total of twenty-seven brain proteins were identified in children with SCD (data not shown). None of these proteins were identified in non-SCD controls. Among the brain proteins identified, Neurogranin had greater than a ten-fold increase in expression in the brain and was found in less than two tissues by EST and SAGE. It also had the highest confidence score and total number of spectral counts.

Plasma Neurogranin Levels in Children.

Figure 9A:
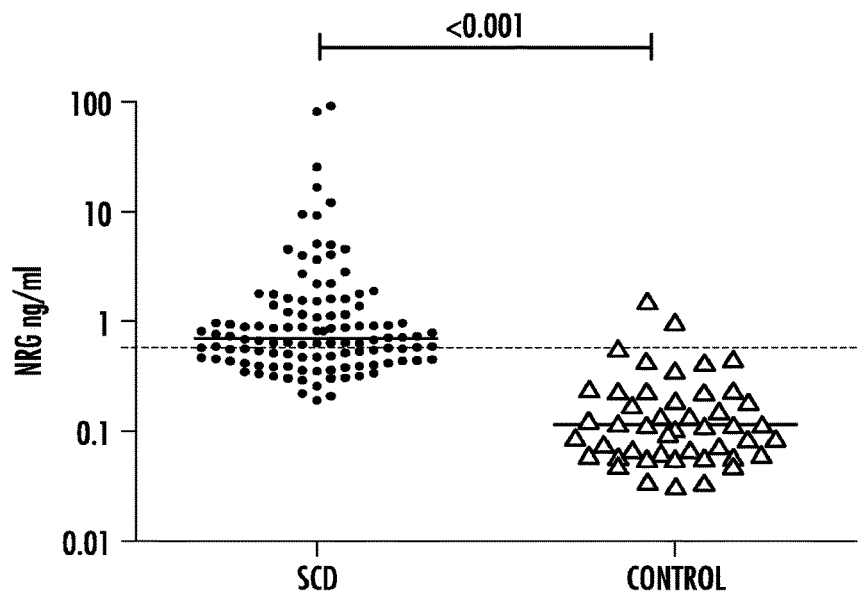
FIG. 9A is a log plot of plasma Neurogranin concentrations in children with sickle cell disease (SCD) (n=115) and age-matched, non-SCD controls (n=46). The dashed line marks the 95th percentile value among 46 non-SCD controls. Bars represent median values.
Figure 9B:
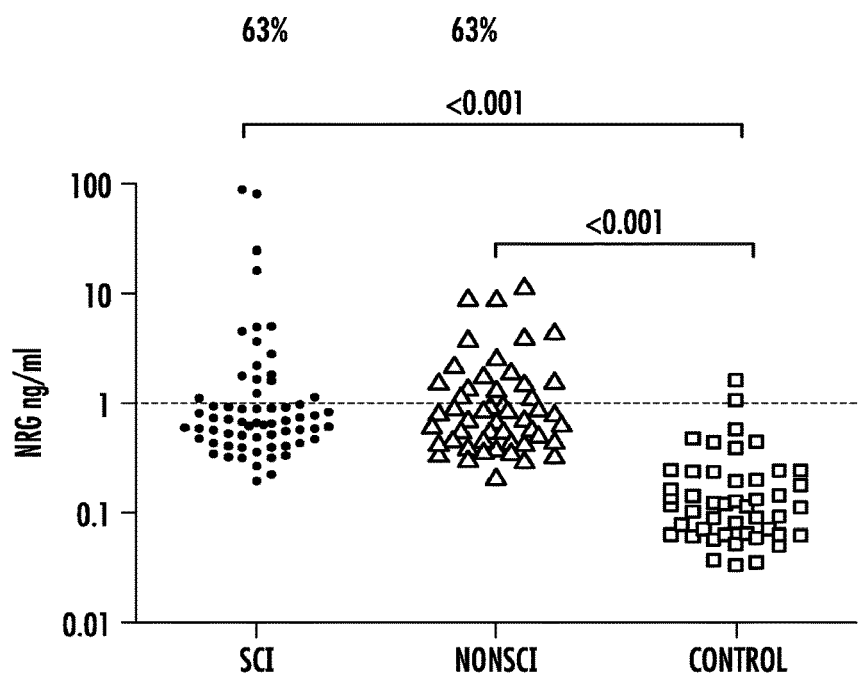
FIG. 9B is a log plot of plasma Neurogranin concentrations in children with SCD and SCI (n=64), with SCD and no SCI (n=51), and age-matched, non-SCD controls (n=46). The dashed line marks the 95th percentile value among 60 healthy pediatric controls, and percentages list the proportions above the 95th percentile of healthy controls.

Neurogranin, a calcium-sensitive calmodulin-binding neuron-specific protein that has been implicated in synaptic development and remodeling, was found in SCD children with and without SCI. As shown in FIG. 9A, median plasma Neurogranin levels were significantly higher in children with SCD (0.72 µg/ml) as compared to non-SCD controls (0.12 µg/ml, P<0.001). Among children with SCD, sixty-three percent of SCI (40/64) and non-SCI (32/51) children had median Neurogranin values that were above the 95$^{th}$ percentile for non-SCD values (FIG. 9B). There were no differences in median Neurogranin levels between the SCI (0.69 µg) and non-SCI groups (0.73, P=0.6, data not shown). Neurogranin did not correlate with known risk factors for SCI, including hb, hct, WBC, platelet, and reticulocyte counts, systolic blood pressure and percent of hb F.

DISCUSSION

Biomarkers of subclinical brain injury in SCD are needed to diagnosis and aid in the development of molecular targeted therapies, as well as to monitor disease response. Proteomics provides an opportunity to discover these biochemical markers in complex mixtures, such as plasma. However, an established methodology for the discovery of brain biomarkers in children with SCD has not been previously reported. A proteomic-based approach was used to test the hypothesis that children with SCD and SCI have brain proteins circulating in their plasma proteome that is associated with subclinical brain injury. Using a workflow of sequential depletion steps, followed by fractionation by RP-HPLC and label-free quantification on a LTQ-Orbitrap mass spectrometer, 1162 proteins were identified and characterized in the children with SCD, of which twenty-seven were found to have high expression in the brain. The experimental approach was validated using an immunoassay developed to measure Neurogranin.

Neurogranin was measured in children with SCD and age-matched, non-SCD controls and found that children with SCD had significantly higher plasma levels of Neurogranin. In fact, greater than sixty percent of SCD children, with and without SCI, had Neurogranin values that were greater than the 95$^{th}$ percentile for observed Neurogranin values in non-SCD controls. Neurogranin has not been previously studied in children with SCD. In fact, previous studies have largely been done in adults with schizophrenia and Alzheimer disease, and have related Neurogranin to impairments in learning and memory. Neurocognitive deficits in academic achievement and memory in children with SCD have been well documented. When compared with siblings and age-matched peers, school-aged SCD children with stroke appeared to have more neuropsychological deficits, but deficits were also found in patients who had clinically mild disease. These findings of increased Neurogranin in children with SCD may be relevant to the etiology of neurocognitive dysfunction, as measured by IQ, as is observed in these patients. Further studies to evaluate whether existing therapies, such as blood transfusions and hydroxyurea, modulate levels of Neurogranin would be informative, and may provide a measurable way to evaluate whether these therapies can help maintain brain function, or perhaps even reverse any loss of function.

In addition, the results from pathway analysis confirm that children with SCD are at risk for neuronal injury and cell death, and suggest specific mechanisms for injury including tauopathy and axonal loss. The analysis suggested that glial fibrillary acidic protein (GFAP), an intracellular intermediate filament protein that is a known biomarker of stroke, is associated with tauopathy in children with SCD and SCI. The present inventors have previously shown that GFAP is elevated in patients with SCD when compared to healthy controls, and is associated with ischemic brain injury, including silent cerebral infarctions.

In summary, the present inventors have developed and verified a proteomic work-flow for brain biomarker discovery in children with SCD. The present inventors are the first to report significant elevations of Neurogranin in children with SCD as compared to age-matched, non-SCD controls, and provide additional insight into the pathophysiology of subclinical brain injury. Collectively, these findings support clinical investigation for biomarker discovery in children with SCD and SCI, and provide new potential targets for therapeutic drug discovery.

We claim:

1. A method of diagnosing brain injury in a patient, the method comprising:
   (a) detecting whether neurogranin biomarker is present in a biological sample obtained from the patient by contacting the sample with isolated monoclonal antibody designated 30.5.2 (ATCC Deposit Designation PTA-123496), or an antigen binding fragment thereof, and detecting binding between the neurogranin biomarker and monoclonal antibody 30.5.2 (ATCC Deposit Designation PTA-123496), or an antigen binding fragment thereof; and
   (b) diagnosing the patient with brain injury when the presence of neurogranin biomarker is detected in the sample.

2. The method of claim 1, wherein the isolated 30.5.2 (ATCC Deposit Designation PTA-123496) monoclonal antibody or an antigen binding fragment thereof specifically binds to amino acids 1-78 of SEQ ID NO: 11.

3. The method of claim 1, wherein the isolated 30.5.2 (ATCC Deposit Designation PTA-123496) monoclonal antibody or an antigen binding fragment thereof is coupled to a detectable substance.

4. The method of claim 3, wherein the isolated 30.5.2 (ATCC Deposit Designation PTA-123496) monoclonal antibody or an antigen binding fragment thereof is coupled to a detectable substance selected from an enzyme, a fluorescent label, a radioisotope, or a chemiluminescent label.

5. The method of claim 1, wherein the binding is detected by an enzyme linked immunosorbent assay (ELISA).

6. The method of claim 1, wherein the binding is detected by a competitive-binding assay, Western blot, a radioimmunoassay, or a fluorescence-activated cell sorting (FACS) assay.

7. The method of claim 1, wherein the biological sample is selected from blood, plasma, serum, cerebrospinal fluid, urine, saliva, stool, synovial fluid, a solid tissue sample, a tissue culture sample or cells derived therefrom.

8. The method of claim 7, wherein the biological sample is selected from blood, plasma, or serum.

9. The method of claim 1, wherein the isolated 30.5.2 (ATCC Deposit Designation PTA-123496) monoclonal antibody or an antigen binding fragment thereof specifically binds to amino acids 55-78 of SEQ ID NO: 11.

10. The method of claim 1, wherein the isolated 30.5.2 (ATCC Deposit Designation PTA-123496) monoclonal antibody or an antigen binding fragment thereof is mammalian.

11. The method of claim 1, wherein the antigen-binding fragment of the isolated 30.5.2 (ATCC Deposit Designation PTA-123496) monoclonal antibody is selected from the group consisting of a Fab fragment, a F(ab')2 fragment, a Fv fragment and a single chain antibody fragment.

12. A method of detecting neurogranin biomarker in a sample, the method comprising:
   (a) contacting a biological sample obtained from a subject with isolated monoclonal antibody designated 30.5.2

(ATCC Deposit Designation PTA-123496), or an antigen binding fragment thereof, wherein the 30.5.2 (ATCC Deposit Designation PTA-123496) monoclonal antibody, or an antigen binding fragment thereof, specifically binds to neurogranin biomarker in the sample; and (b) detecting the neurogranin biomarker by detecting a complex formed by the specific binding of the 30.5.2 (ATCC Deposit Designation PTA-123496) monoclonal antibody, or an antigen binding fragment thereof, to neurogranin biomarker in the sample by a binding assay, an immunoassay, or a cell sorting assay.

13. The method of claim 12, wherein detecting the neurogranin biomarker in the sample diagnoses the subject as having brain injury.

14. The method of claim 12, wherein the biological sample is selected from blood, plasma, serum, cerebrospinal fluid, urine, saliva, stool, synovial fluid, a solid tissue sample, a tissue culture sample or cells derived therefrom.

15. The method of claim 12, wherein the complex is detected by an enzyme linked immunosorbent assay (ELISA).

* * * * *

SEQUENCE LISTING

```
<160> NUMBER OF SEQ ID NOS: 11

<210> SEQ ID NO 1
<211> LENGTH: 82
<212> TYPE: DNA
<213> ORGANISM: Artificial Sequence
<220> FEATURE:
<223> OTHER INFORMATION: Single strand DNA oligo pool with 40mer random
      central core.
<220> FEATURE:
<221> NAME/KEY: misc_feature
<222> LOCATION: (26)..(65)
<223> OTHER INFORMATION: n is a, c, g, or t

<400> SEQUENCE: 1
tctcggatcc tcagcgagtc gtctgnnnnn nnnnnnnnnn nnnnnnnnnn nnnnnnnnnn     60
nnnnnccgca tcgtcctccc ta                                             82

<210> SEQ ID NO 2
<211> LENGTH: 42
<212> TYPE: DNA
<213> ORGANISM: Artificial Sequence
```

```
<220> FEATURE:
<223> OTHER INFORMATION: Sel2 5' primer containing a T7 promoter for in
      vitro transcription.

<400> SEQUENCE: 2
gggggaattc taatacgact cactataggg aggacgatgc gg                        42

<210> SEQ ID NO 3
<211> LENGTH: 23
<212> TYPE: DNA
<213> ORGANISM: Artificial Sequence
<220> FEATURE:
<223> OTHER INFORMATION: Sel2 3' primer.

<400> SEQUENCE: 3
tctcggatcc tcagcgagtc gtc                                            23

<210> SEQ ID NO 4
<211> LENGTH: 40
<212> TYPE: DNA
<213> ORGANISM: Homo sapiens

<400> SEQUENCE: 4
tctaacgcct cccgtatgtt ttccttttt cattgcggat                            40

<210> SEQ ID NO 5
<211> LENGTH: 40
<212> TYPE: DNA
<213> ORGANISM: Homo sapiens

<400> SEQUENCE: 5
tctaacgcct cccgcatgtt ttccttttt cattgcggat                            40

<210> SEQ ID NO 6
<211> LENGTH: 43
<212> TYPE: DNA
<213> ORGANISM: Homo sapiens

<400> SEQUENCE: 6
ttttcatttt cattttttc caaatcgatc cgccggacct tat                        43

<210> SEQ ID NO 7
<211> LENGTH: 14
<212> TYPE: PRT
<213> ORGANISM: Homo sapiens

<400> SEQUENCE: 7

Gly Pro Gly Pro Gly Gly Pro Gly Gly Ala Gly Val Ala Arg
1               5                   10

<210> SEQ ID NO 8
<211> LENGTH: 15
<212> TYPE: PRT
<213> ORGANISM: Homo sapiens

<400> SEQUENCE: 8

Lys Gly Pro Gly Pro Gly Gly Pro Gly Gly Ala Gly Val Ala Arg
1               5                   10                  15

<210> SEQ ID NO 9
<211> LENGTH: 33
<212> TYPE: DNA
<213> ORGANISM: Artificial Sequence
<220> FEATURE:
<223> OTHER INFORMATION: Forward primer for cloning neurogranin
```

```
<400> SEQUENCE: 9
gaggcgatcg ccatggactg ctgcaccgag aac                                   33

<210> SEQ ID NO 10
<211> LENGTH: 29
<212> TYPE: DNA
<213> ORGANISM: Artificial Sequence
<220> FEATURE:
<223> OTHER INFORMATION: Reverse primer for cloning neurogranin

<400> SEQUENCE: 10
gcgacgcgtc tagtctccgc tggggccgc                                        29

<210> SEQ ID NO 11
<211> LENGTH: 78
<212> TYPE: PRT
<213> ORGANISM: Homo sapiens
<220> FEATURE:
<221> NAME/KEY: MISC_FEATURE
<222> LOCATION: (1)..(78)
<223> OTHER INFORMATION: Amino acid sequence of human neurogranin

<400> SEQUENCE: 11

Met Asp Cys Cys Thr Glu Asn Ala Cys Ser Lys Pro Asp Asp Ile
1               5                   10                  15

Leu Asp Ile Pro Leu Asp Asp Pro Gly Ala Asn Ala Ala Ala Ala Lys
                20                  25                  30

Ile Gln Ala Ser Phe Arg Gly His Met Ala Arg Lys Lys Ile Lys Ser
            35                  40                  45

Gly Glu Arg Gly Arg Lys Gly Pro Gly Pro Gly Pro Gly Gly Ala
    50                  55                  60

Gly Val Ala Arg Gly Gly Ala Gly Gly Gly Pro Ser Gly Asp
65                  70                  75
```